US012606539B2

(12) United States Patent
Hylse et al.

(10) Patent No.: US 12,606,539 B2
(45) Date of Patent: Apr. 21, 2026

(54) PROCESS FOR PREPARATION OF APALUTAMIDE

(71) Applicant: Synthon B.V., Nijmegen (NL)

(72) Inventors: Ondrej Hylse, Blansko (CZ); David Chalupa, Blansko (CZ); Bohumil Dymacek, Blansko (CZ); Marian Buchlovic, Blansko (CZ)

(73) Assignee: Synthon B.V., Nijmegen (NL)

( * ) Notice: Subject to any disclaimer, the term of this patent is extended or adjusted under 35 U.S.C. 154(b) by 539 days.

(21) Appl. No.: 18/043,777

(22) PCT Filed: Sep. 3, 2021

(86) PCT No.: PCT/EP2021/074415
§ 371 (c)(1),
(2) Date: Mar. 2, 2023

(87) PCT Pub. No.: WO2022/049265
PCT Pub. Date: Mar. 10, 2022

(65) Prior Publication Data

US 2023/0312507 A1 Oct. 5, 2023

(30) Foreign Application Priority Data

Sep. 4, 2020 (EP) .................................... 20194708
Mar. 12, 2021 (EP) .................................... 21162371
Jun. 10, 2021 (EP) .................................... 21178778

(51) Int. Cl.
*C07D 401/04* (2006.01)
*C07C 229/48* (2006.01)

(52) U.S. Cl.
CPC .......... *C07D 401/04* (2013.01); *C07C 229/48* (2013.01)

(58) Field of Classification Search
CPC ............................ C07D 401/04; C07C 229/48
USPC ....................................................... 546/268.4
See application file for complete search history.

(56) References Cited

U.S. PATENT DOCUMENTS

2018/0201601 A1 7/2018 Chen et al.
2020/0024250 A1 1/2020 Singh et al.

FOREIGN PATENT DOCUMENTS

| | | | | |
|---|---|---|---|---|
| WO | WO2007126765 A2 | 11/2007 | | |
| WO | WO2008/119015 A2 | 10/2008 | | |
| WO | WO2013184681 A1 | 12/2013 | | |
| WO | WO2016100645 | 6/2016 | | |
| WO | WO2016100652 | 6/2016 | | |
| WO | WO2018112001 A1 | 6/2018 | | |
| WO | WO2018136001 A1 | 7/2018 | | |
| WO | WO2019135254 A1 | 7/2019 | | |
| WO | WO-2019229625 A1 * | 12/2019 | ............ | C07F 7/1896 |
| WO | WO2019242439 A1 | 12/2019 | | |

* cited by examiner

*Primary Examiner* — Kahsay Habte
(74) *Attorney, Agent, or Firm* — Buscher Patent PLLC

(57) ABSTRACT

The presented invention relates to a process for preparation of Apalutamide, compound (1) or a salt or a solvate thereof:

(1)

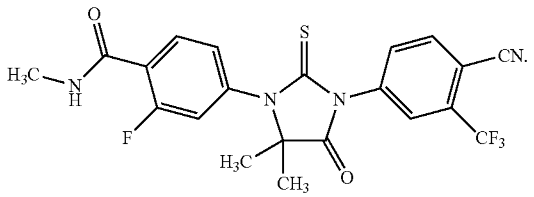

The presented invention further relates to solid forms of Apalutamide, solvates of Apalutamide and to processes for preparation thereof. The presented invention also relates to solid forms of intermediates used in the process for preparing Compound (1).

14 Claims, 18 Drawing Sheets

PROCESS FOR PREPARATION OF APALUTAMIDE

The presented invention relates to an improved process for preparation of compound of formula (1). i.e. Apalutamide or a salt thereof.

(1)

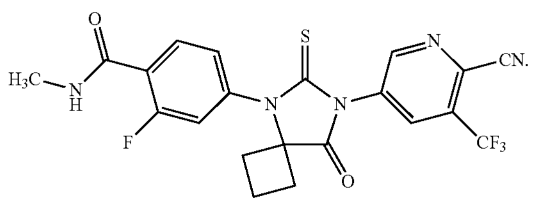

The presented invention also relates to solid forms of intermediates used in the process for preparing Compound (1). The presented invention further relates to solid forms of Apalutamide, solvates of Apalutamide and to processes for preparation thereof.

BACKGROUND OF THE PRESENT INVENTION

Apalutamide, compound of formula (1), (1)

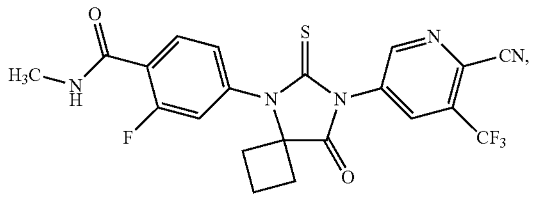

chemically 4-[7-[6-Cyano-5-(trifluoromethyl)pyridin-3-yl]-8-oxo-6-thioxo-5,7-diazaspiro[3.4]oct-5-yl]-2-fluoro-N-methylbenzamide is an androgen receptor antagonist, that is useful for treatment of non-metastatic castration-resistant prostate cancer.

Apalutamide was first disclosed in WO2007126765A2 by The University of California. The application also describes a process for preparation of Apalutamide. The disadvantages of disclosed process are use of toxic reagents (sodium cyanide) and use of microwave heating that is unsuitable for larger scale production. Several other processes for preparation of Apalutamide are disclosed in the prior art. The processes described in WO2016100652 and WO2016100645, both by Aragon Pharmaceuticals are relatively long and use toxic reagents (phosgene, sodium cyanide). The process disclosed in WO2008/119015A2 by Sloan-Kettering Institute for Cancer Research also uses toxic reagents (thiophosgene, sodium cyanide) and additionally to that it uses microwave radiation that is unsuitable for larger scale production. The disadvantage of processes disclosed in WO2018136001A1 by ScinoPharm and WO2019229625A1 by Olon is use of excess of 5-isothiocyanato-3-(trifluoromethyl)picolinonitrile that is a reactive compound. That together with relatively high reaction temperature results in relatively low purity of the product that needs to be purified by column chromatography.

There is therefore a need for improved process for preparation of Apalutamide with relatively short reaction times and good yields and purity of intermediates and Apalutamide that does not comprise toxic reagents and does not require column chromatography for purification of either an intermediate or Apalutamide.

Solid forms of Apalutamide are disclosed for example in WO20131846814A1 by Aragon Pharmaceuticals or WO2018112001A1 by Watson Laboratories or WO2019135254A1 by Mylan or WO2019242439A1 (Crystal Pharmaceutical).

There is still a need for solid forms of Apalutamide with improved properties such as crystallinity or stability.

SUMMARY OF THE INVENTION

The presented invention relates to a process for preparation of Compound (1), i.e. Apalutamide, or a salt thereof;

(1)

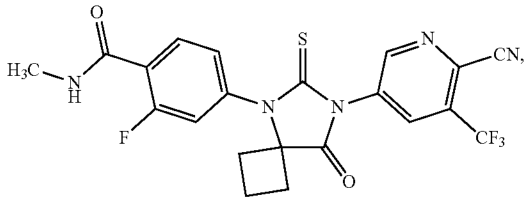

comprising:

a. Reacting Compound (2) with Compound (3) in a presence of a non-nucleophilic base to obtain Compound (4), wherein the $pK_a$ value of conjugated acid formed from the non-nucleophilic base is higher than 25.

(2)

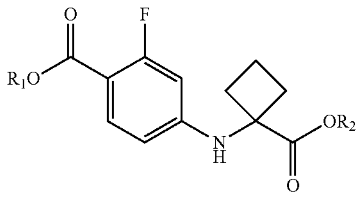

(3)

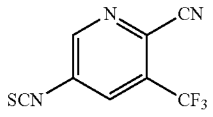

(4)

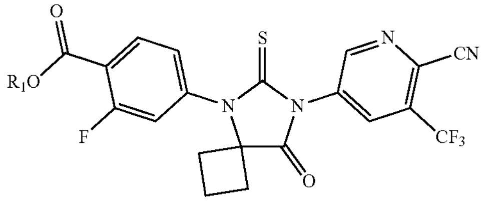

$R_1$ is selected from $C_1$-$C_6$ alkyl or substituted $C_1$-$C_6$ alkyl or aryl or substituted aryl $R_2$ is selected from alkyl or substituted alkyl or aryl or substituted aryl or $C(O)R_3$ or $C(O)OR_3$ $R_3$ is selected from $C_1$-$C_6$ alkyl or substituted $C_1$-$C_6$ alkyl or aryl or substituted aryl;

b. Transforming Compound (4) into Compound (1).

The presented invention further relates to a process for isolation of a solid form of Compound (1) or solvates thereof. The presented invention also relates to solid forms of intermediates used in the process for preparing Compound (1).

The presented invention also relates to a solid form of Apalutamide 2-propanol solvate, Form 7, characterized by XRPD pattern having 2θ values 4.6°, 7.1°, 13.8° and 16.0° 2θ (±0.2 degrees 2θ).

The presented invention further relates to a solid form of Apalutamide 1-methoxy-2-propanol solvate, Form 5, characterized by XRPD pattern having 2θ values 4.7°, 7.1° and 13.9° 2θ (±0.2 degrees 2θ).

The presented invention also relates to a solid form of Apalutamide, Form 3, characterized by:

a. XRPD pattern having 2θ values 4.7°, 7.1°, 13.3°, 13.8° and 14.2° 2θ (±0.2 degrees 2θ); and b. DSC pattern with an endotherm having an onset temperature at about 111.9°-115.9° C. and a peak at about 118.6° C.-120.3° C.

The presented invention also relates to a solid form of Apalutamide methyl isobutyl ketone solvate, Form 6, characterized by XRPD pattern having 2θ values 3.8°, 6.9°, 8.8°, 16.2° and 20.8° 2θ (±0.2 degrees 2θ).

DETAILED DESCRIPTION OF THE INVENTION

Figure 1:
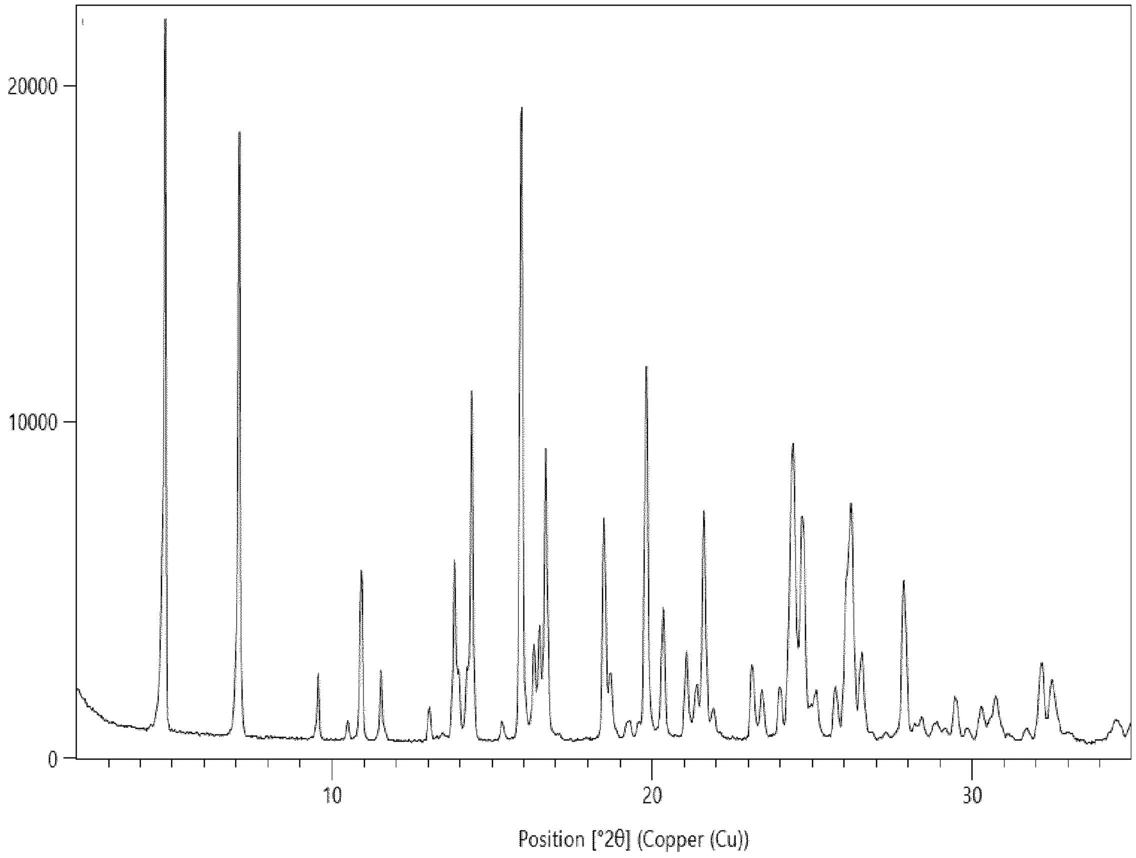
FIG. 1: XRPD pattern of solid form of methyl 4-(7-(6-cyano-5-(trifluoromethyl-) pyridin-3-yl)-8-oxo-6-thioxo-5,7-diazaspiro[3.4]octan-5-yl)-2-fluorobenzoate prepared according to Example 3.

In the following text "Compound (number)" means compound of formula (number).

The presented invention relates to a process for preparation of Apalutamide, i.e. Compound (1) or a salt thereof, (1)

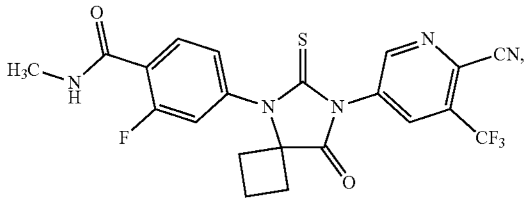

comprising:

a. Reacting Compound (2) with Compound (3) in a presence of a non-nucleophilic base to obtain Compound (4), wherein the $pK_a$ value of conjugated acid formed from the non-nucleophilic base is higher than 25;

(2)

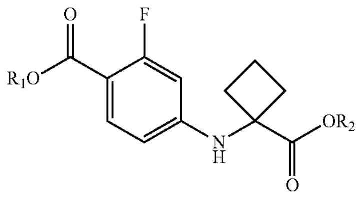

(3)

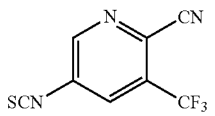

(4)

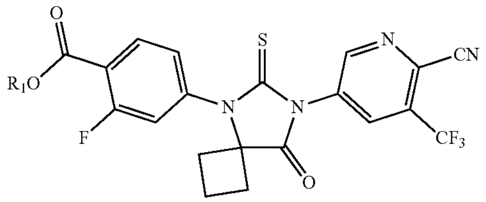

$R_1$ is selected from $C_1$-$C_6$ alkyl or substituted $C_1$-$C_6$ alkyl or aryl or substituted aryl $R_2$ is selected from alkyl or substituted alkyl or aryl or substituted aryl or $C(O)R_3$ or $C(O)OR_3$ $R_3$ is selected from $C_1$-$C_6$ alkyl or substituted $C_1$-$C_6$ alkyl or aryl or substituted aryl;

b. Transforming Compound (4) into Compound (1).

$R_1$ and $R_2$ are preferably selected from $C_1$-$C_6$ alkyl or substituted $C_1$-$C_6$ alkyl, more preferably are both $CH_3$. The non-nucleophilic base (i.e. sterically hindered organic base that is a poor nucleophile) used in step a. can be selected from lithium bis(trimethylsilyl)amide or sodium bis(trimethylsilyl)amide or potassium bis(trimethylsilyl)amide or sodium hydride or potassium hydride or lithium diisopropylamide or lithium diethylamide or lithium dicyclohexylamide or lithium 2,2,6,6-tetramethylpiperidine or Hauser bases ($(R)_2NMgX$, R can be selected from for example isopropyl or cyclohexyl or 2,2,6,6-tetramethylpiperidinyl, X means a halogenide) or turbo-Hauser bases ($(R)_2NMgX$—LiCl, R can be selected from for example isopropyl or cyclohexyl or 2,2,6,6-tetramethylpiperidinyl, X means a halogenide), preferably the base is lithium bis(trimethylsilyl)amide or sodium bis(trimethylsilyl)amide or potassium bis(trimethylsilyl)amide. We have surprisingly found that when a non-nucleophilic base is used wherein the $pK_a$ value of conjugated acid formed from the non-nucleophilic base is higher than 25, the reaction can be performed under mild conditions and Compound (3) can be used in very low excess. Higher excess of Compound (3) used in reaction as same as higher reaction temperatures result in formation of impurities in Compound (4) that need to be purified before transformation of Compound (4) into Compound (1) and that are difficult to purify.

The molar ration between the Compound (3) and the Compound (2) can be between 1:1.1 and 1:2, preferably it is between 1:1.1 and 1:1.3, more preferably it is between 1:1.02 and 1:1.04. The molar ratio between the non-nucleophilic base and the Compound (2) can be between 1:0.8 and 1:2, preferably it is between 1:0.9 and 1:1.5. The reaction step a. can be performed in a suitable solvent. The solvent can be selected from dimethylformamide (DMF) or tetrahydrofuran or 2-methyltetrahydrofurane or a mixture thereof, preferably it is tetrahydrofuran. The reaction step a. can be performed under a protective atmosphere, for example using argon or nitrogen atmosphere.

Compound (2) is mixed with used solvent or solvent mixture. The mixture can be then cooled, for example to a temperature between −10° C. and 15° C., preferably to a temperature between −10° C. and 12° C. The non-nucleophilic base is the added to the mixture. The non-nucleophilic base can be added in form of a solution in a suitable solvent, for example the solvent used in the reaction such as tetrahydrofuran, or it can be added as solid. The non-nucleophilic base can be added in parts, for example in 2 or 3 or 4 or 5 or 6 parts. In case the non-nucleophilic base is used in form of a solution it can be added drop-wise. The temperature of the mixture while base addition can be preferably maintained between 0° C. and 15° C., preferably between 0° C. and 5° C. After base addition, the mixture can be stirred for between 5 and 60 minutes at a temperature between −10° C. and 15° C., preferably between −10° C. and 0° C. To the mixture a solution of Compound (3) is then added. Compound (3) can be dissolved for example in the solvent used in the reaction, for example in tetrahydrofuran. The solution of Compound (3) can be added in several parts, for example in 2 or 3 or 4 or 5 or 6 parts, preferably it is added drop-wise. The temperature of the mixture while addition of Compound (3) can be preferably maintained between −10° C. and 15° C., preferably between −10° C. and 0° C. C and the mixture can be optionally stirred at this temperature for between 5 and 120 minutes, preferably for between 5 and 30 minutes. The reaction progress can be monitored by a suitable analytical technique, e.g. by HPLC or GC.

After the reaction is finished to the mixture an organic solvent non-miscible with water, for example an ether such as diethyl ether or methyl tert-butyl ether is added. The addition of the non-miscible solvent improves the processing of the mixture in subsequent steps. The volume ratio between the solvent used in step a. and the water non-miscible organic solvent can be between 1.5:1 and 2.5:1, preferably it is between 1.6:1 and 2:1. To the mixture a water solution of an acid, for example hydrochloric acid, is added. The molar ration between the acid and the Compound (2) can be between 1:2 and 1:5. The temperature of the mixture while acid addition is maintained at a temperature below 20° C. The phases are separated. The washing step of the organic phase with the water solution of an acid can be repeated, for example 2 or 3 times. The organic phases can be then treated with active carbon for between 20 and 120 minutes. The weight ratio between the Compound (2) and the active carbon can be between 15:1 and 25:1. After the treatment, the mixture is filtered. To the filtrate a water miscible solvent for example an alcohol, such as ethanol or 1-propanol or 2-propanol or 2-butanol or isobutanol or 1-butanol, preferably 2-propanol, is added. The volume ratio between added solvent and the solvent used in step a. can be between 1:1 and 1:1.3. The mixture is concentrated at an elevated temperature to approximately ½ of the original volume and the mixture is cooled to a temperature between 20° C. and 25° C. to obtain a suspension. The suspension is stirred at a temperature between 20° C. and 25° C. for between 30 minutes and 180 minutes. The mixture is filtrated and obtained solid Compound (4) can be dried.

The Compound (4) can be also isolated by following process. After the reaction is finished, the reaction mixture is cooled to a temperature between −10° C. and −5° C. To the mixture an acid, for example HCl, is added. Concentration of the acid can be between 0.04 g/ml and 0.15 g/ml. The molar ratio between the acid and the Compound (2) can be between 1.8:1 and 3:1, preferably it is between 2:1 and 2.5:1. The mixture is heated to a temperature between 25° C. and 35° C. and the phases are separated. The organic phase was washed with 20% aqueous solution of NaCl (volume ratio between NaCl solution and the organic phase is approximately 3:1) and the layers were separated. The organic layer is concentrated to ½ of the original volume and the solvent was switched to methanol using sequential addition and distillation of methanol. Then the mixture is concentrated to ½ of the original volume. To the mixture isopropanol is added. The weight ratio between added isopropanol and methanol used for solvent switch can be between 1:2 and 1:3, preferably it is between 1:2.5 and 1:2.8. The mixture is heated to reflux and stirred at this temperature for between 15 and 45 minutes. The mixture is cooled to a temperature between −10° C. and 0° C. and stirred at this temperature for between 20 and 60 minutes to obtain a suspension. The suspension is filtered off and the filtration cake can be optionally washed with a suitable solvent for example with aqueous methanol and dried to provide compound (4).

The Compound (4) can be further purified by crystallization from a solvent selected from 1-propanol or 2-propanol or 2-butanol or isobutanol or 1-butanol, preferably 2-propanol. The Compound (4) is mixed with the solvent. The concentration of Compound (4) in the solvent can be between 0.06 g/ml and 0.2 g/ml, preferably it is between 0.08 g/ml and 0.15 g/ml. The mixture can be heated, preferably to a reflux temperature of used solvent to dissolve the Compound (4). The mixture can be then cooled to a temperature between 50° C. and 80° C. and stirred at this temperature for between 1 and 10 hours. The mixture is then cooled to a temperature between 20° C. and 25° C. and stirred at this temperature for between 2 and 15 hours. The obtained solid Compound (4) is then filtered off and optionally dried.

In case $R_1$ in $CH_3$, Compound (4) corresponds to the following formula:

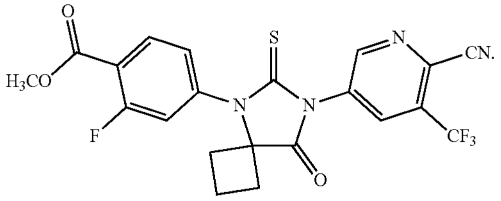 [SMILES: COC(=O)c1ccc(N2C(=S)N(c3cnc(C#N)c(C(F)(F)F)c3)C(=O)C23CCC3)cc1F]

The obtained solid form can be characterized by XRPD pattern having 2θ values 4.8°, 7.1° and 15.9° 2θ (±0.2 degrees 2θ). The solid form can be also characterized by XRPD pattern having 2θ values 4.8°, 7.10, 10.9°, 14.4° and 15.9° 2θ (±0.2 degrees 2θ). The solid form can be further characterized by XRPD pattern described in following Table:

| Angle 2-Theta° | Intensity % |
|---|---|
| 4.8 | 100.0 |
| 7.1 | 86.8 |
| 9.6 | 11.7 |
| 10.5 | 5.2 |
| 10.9 | 27.3 |
| 11.5 | 12.0 |
| 13.0 | 6.9 |
| 13.4 | 3.3 |
| 13.8 | 28.8 |
| 14.4 | 52.5 |
| 15.3 | 4.9 |
| 15.9 | 92.6 |
| 16.3 | 15.2 |
| 16.5 | 18.6 |
| 16.7 | 41.8 |
| 18.5 | 33.3 |
| 18.7 | 11.5 |
| 19.3 | 5.1 |
| 19.6 | 4.9 |
| 19.8 | 54.0 |
| 20.4 | 20.2 |
| 21.1 | 14.4 |
| 21.4 | 10.1 |
| 21.6 | 34.3 |
| 21.9 | 6.8 |
| 23.1 | 12.5 |
| 23.4 | 9.3 |
| 24.0 | 9.8 |
| 24.4 | 42.6 |
| 24.7 | 32.9 |
| 25.1 | 9.1 |
| 25.7 | 9.6 |
| 26.1 | 24.7 |
| 26.2 | 34.6 |
| 26.5 | 14.6 |
| 27.3 | 3.6 |
| 27.9 | 24.1 |
| 28.2 | 4.6 |
| 28.4 | 5.5 |
| 28.9 | 5.0 |
| 29.1 | 4.1 |
| 29.5 | 8.2 |
| 29.8 | 4.0 |

-continued

| Angle 2-Theta° | Intensity % |
|---|---|
| 30.3 | 6.8 |
| 30.7 | 8.3 |
| 31.1 | 3.3 |
| 31.7 | 4.0 |
| 32.2 | 12.8 |
| 32.5 | 10.7 |
| 33.0 | 3.6 |
| 34.0 | 2.6 |
| 34.5 | 5.2 |

The solid form can be also characterized by XRPD pattern depicted in FIG. 1.

The Compound (4) can be transformed into Compound (1), i.e. Apalutamide, for example by a process comprising reacting the Compound (4) with methylamine or a salt thereof. The reaction can be performed in a suitable solvent for example tetrahydrofuran (THF) or 2-methyl tetrahydrofuran (2-Me THF). Methylamine or the salt thereof can be used in a form of water solution, for example 10% or 20% or 30% or 40% or 5000 solution. The concentration of Compound (4) in the solvent can be between 0.3 g/ml and 1 g/ml, preferably it is between 0.3 g/ml and 0.5 g/ml. The molar ratio between Compound (4) and methylamine or a salt thereof can be between 1:20 and 1:30, preferably it is between 1:23 and 1:27. Compound (4) is mixed with the solvent and the mixture is added to methylamine or a solution thereof at a temperature between −10° C. and 10° C. slowly, i.e. in the course of 5 or 10 or 20 or 30 or 40 or 50 or 60 minutes or drop-wise. The mixture is stirred at the same temperature for between 2 and 5 hours. The reaction progress can be monitored by a suitable analytical technique, e.g. by HPLC or GC. After the reaction is finished, to the mixture a solution of an acid in an alcohol is added, for example 6M HCl in isopropanol or a solution of acetic acid in water can be used. The concentration of the acetic acid in water can be between 1 g/ml and 2 g/ml, preferably it is between 1.1 g/ml and 1.5 g/ml. The molar ration between the acid, preferably HCl or acetic acid, and compound of formula (4) can be between 20:1 and 30:1, preferably it is between 23:1 and 27:1. In the case when HCl is used during the addition a suspension is formed. The suspension can be stirred for between 10 and 60 minutes and filtered. The obtained solid can be optionally dried to provide Compound (1).

In the case when acetic acid is used the acid is added slowly, for example in the course of between 15 and 40 minutes. The temperature of the mixture is maintained between 0° C. and 20° C. during the addition. After the acid is added the mixture is heated to a temperature between 25° C. and 30° C. The phases are separated and to the organic phase an aqueous solution of a carbonate, for example sodium or potassium carbonate is added. The phases are separated and to the organic phase an aqueous solution of a carbonate, for example sodium or potassium carbonate is added. The phases are separated. To the organic phase an aqueous solution of acetic acid was added. The concentration of acetic acid can be between 1 and 3% (wt/wt). The weight ratio between added acetic acid and Compound (4) can be between 1.9:1 and 2.5:1, preferably it is between 1.9:1 and 2.2:1. The mixture is heated to a temperature between 55° C. and 65° C. and 2-propanol is added. The weight ratio between 2-propanol and added acetic acid can be between 1:2 and 1:3, preferably it is between 1:2.2 and 1:2.8. The phases are separated. To the organic phase 2-propanol is added. Weight ratio between added 2-propanol and 2-propanol added in the previous step can be between 6.5:1 and 7:5:1. The mixture was heated to reflux and stirred at this temperature for between 10 and 45 minutes. The mixture was cooled to a temperature between −10° C. and 0° C. during between 2 and 4 hours. The mixture was stirred at this temperature for between 20 and 60 minutes, solid mass was filtered off and optionally washed with cold 2-propanol and dried to obtain a solid form of Apalutamide, Compound (1), preferably in solid Form 7.

The Compound (2) can be prepared by a process comprising reacting Compound (5) with an acid and alcohol $R_2OH$, $R_2$ can be selected from alkyl or substituted alkyl or aryl or substituted aryl or $C(O)R_3$ or $C(O)OR_3$, $R_3$ can be selected from $C_1$-$C_6$ alkyl or substituted $C_1$-$C_6$ alkyl or aryl or substituted aryl:

(5)

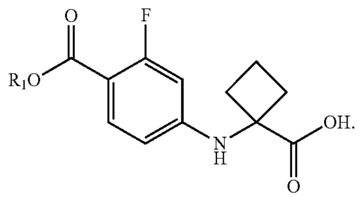

$R_1$ is selected from $C_1$-$C_6$ alkyl or substituted $C_1$-$C_6$ alkyl or aryl or substituted aryl, preferably it is $CH_3$.

The acid can be selected from for example sulfuric acid or toluene sulfonic acid. The alcohol can be selected from methanol or ethanol or propanol or 2-propanol or butanol, preferably it is methanol. Compound (5) is mixed with the alcohol. The concentration of Compound (5) in the alcohol can be between 0.1 g/ml and 0.3 g/ml, preferably it is between 0.12 g/ml and 0.25 g/ml. To the mixture the acid is slowly added, for example in 2 or 3 or 4 or 5 or 6 parts, preferably it is added drop-wise. The mixture is then heated to a temperature between 50° C. and the reflux temperature of used solvent and stirred at this temperature for between 2 and 10 hours, preferably between 3 and 6 hours. The reaction progress can be monitored by a suitable analytical technique, e.g. by HPLC or GC. After the reaction is finished the mixture is cooled to a temperature between 15° C. and 30° C., preferably between 20° C. and 35° C., more preferably between 30° C. and 35° C. To the mixture a water solution of a base is slowly added, preferably in the course between 10 and 120 minutes. As a base a hydroxide such as sodium hydroxide or potassium hydroxide or a carbonate such as sodium carbonate or potassium carbonate or a hydrogen carbonate such as sodium hydrogen carbonate or potassium hydrogen carbonate or an organic base for example trimethylamine or triethylamine or diisopropylethyl amine can be used. Preferably triethylamine or sodium carbonate is used. In the case when base a hydroxide such as sodium hydroxide or potassium hydroxide or a carbonate such as sodium carbonate or potassium carbonate or a hydrogen carbonate such as sodium hydrogen carbonate or potassium hydrogen carbonate is used as a base the molar ratio between acid and the base can be between 0.5:1 and 1:1, preferably it is 1:1. In the case an organic base, preferably triethylamine, is used as a base, the concentration of the base in water can be between 0.4 g/ml and 0.8 g/ml and the molar ratio between acid and the base can be between 1:3 and 1:5, preferably it is between 1:3 and 1:4.

The mixture can be optionally cooled to a temperature between −10° C. and 0° C. The mixture is stirred for between 30 minutes and 180 minutes. Obtained suspension is filtered off and obtained Compound (2) can be dried.

In a case both $R_1$ and $R_2$ are $CH_3$, Compound (2) corresponds to the following formula:

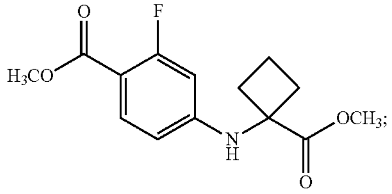 [SMILES: COC(=O)c1ccc(NC2(C(=O)OC)CCC2)cc1F]

and the obtained solid form can be characterized by XRPD pattern having 2θ values 10.2°, 14.5° and 17.4° 2θ (±0.2 degrees 2θ). The solid form can be also characterized by XRPD pattern having 2θ values 10.2°, 14.5°, 15.2°, 17.4° and 19.0° 2θ (±0.2 degrees 2θ). The solid form can be further characterized by XRPD pattern described in following Table:

| Angle 2-Theta° | Intensity % |
|---|---|
| 10.2 | 100.0 |
| 12.3 | 21.9 |
| 13.6 | 13.5 |
| 14.5 | 69.3 |
| 15.2 | 25.2 |
| 15.5 | 15.6 |
| 16.7 | 3.9 |
| 17.4 | 58.1 |
| 17.6 | 24.7 |
| 18.1 | 15.0 |
| 19.0 | 50.2 |
| 19.3 | 3.8 |
| 19.6 | 17.8 |
| 20.4 | 7.5 |
| 20.8 | 18.3 |
| 21.3 | 21.2 |
| 22.0 | 69.0 |
| 22.5 | 8.1 |
| 23.0 | 3.8 |
| 23.2 | 10.5 |
| 23.8 | 13.2 |
| 24.7 | 26.7 |
| 25.1 | 5.2 |
| 25.5 | 30.5 |
| 25.9 | 3.2 |
| 26.1 | 5.8 |
| 26.7 | 8.3 |
| 27.3 | 51.3 |
| 28.0 | 8.1 |
| 28.4 | 1.9 |
| 28.9 | 3.2 |
| 29.1 | 4.4 |
| 30.2 | 5.4 |
| 30.5 | 2.4 |
| 30.9 | 17.8 |
| 31.4 | 3.0 |
| 31.7 | 6.2 |
| 32.0 | 4.3 |
| 32.3 | 4.4 |
| 32.8 | 2.0 |
| 33.1 | 2.6 |
| 33.5 | 2.5 |
| 33.7 | 2.5 |
| 34.4 | 1.9 |
| 34.8 | 2.4 |

Figure 3:
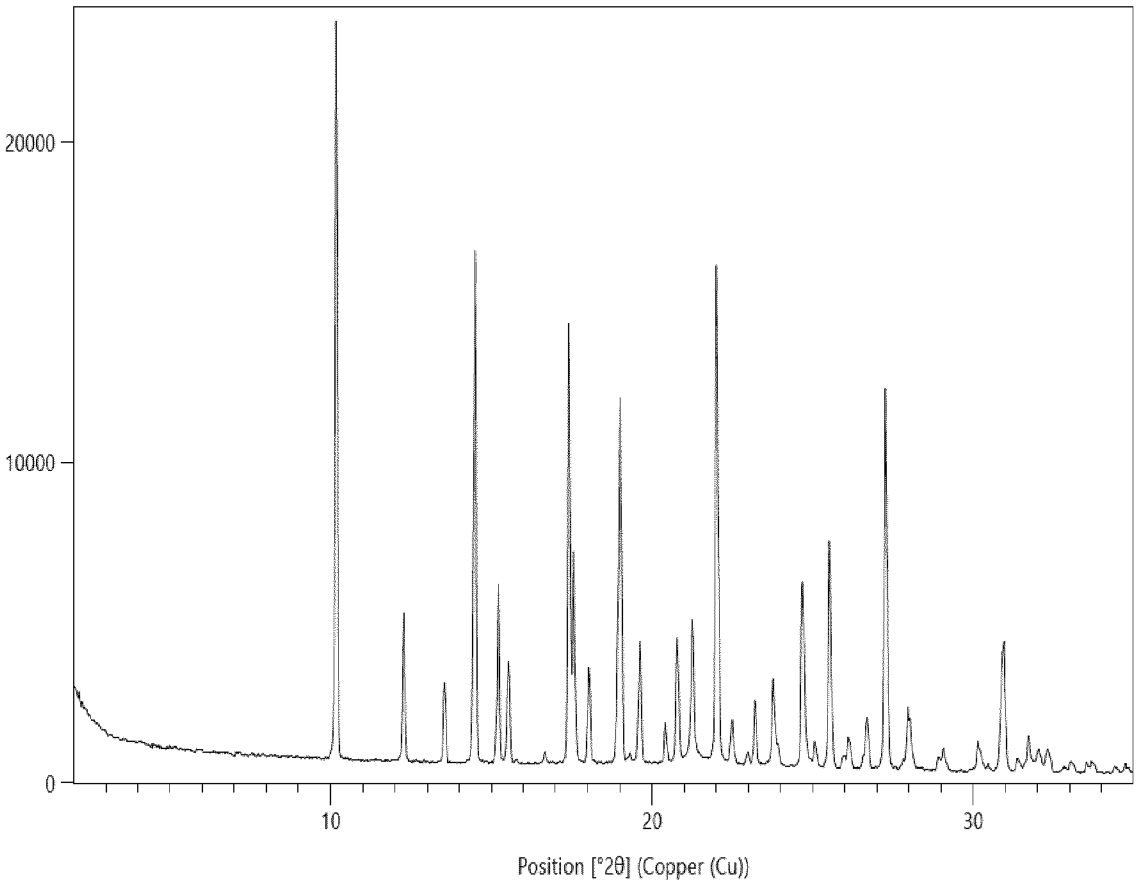
FIG. 3: XRPD pattern of solid form of methyl 2-fluoro-4-((1-(methoxycarbonyl)cyclobutyl)amino)benzoate prepared according to Example 2.

The solid form can be also characterized by XRPD pattern depicted in FIG. 3.

The Compound (5) can be prepared reacting Compound (6) and Compound (7) or a salt thereof under a protective gas wherein the protective gas is optionally streamed above the reaction mixture:

(6)

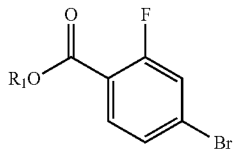

(7)

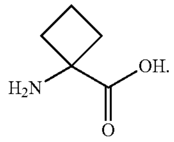

$R_1$ is selected from $C_1$-$C_6$ alkyl or substituted $C_1$-$C_6$ alkyl or aryl or substituted aryl, preferably it is $CH_3$.

Compounds (6) and (7) are commercially available.

The reaction can be done in a suitable solvent such as dimethylsulfoxide (DMSO) or dimethylformamide (DMF) or dimethylacetamide (DMAC), preferably dimethylsulfoxide or dimethylformamide is used. Compound (7) can be used in a form of a salt for example HCl salt. The molar ration between Compound (6) and Compound (7) can be between 1:1.3 and 1:2, preferably it is between 1:1.4 and 1:1.6. The concentration of Compound (6) in the solvent can be between 0.1 g/ml and 0.4 g/ml, preferably it is between 0.25 g/ml and 0.35 g/ml. The concentration of Compound (7) in the solvent can be between 0.1 g/ml and 0.35 g/ml, preferably it is between 0.25 g/ml and 0.31 g/ml. The reaction is done in a presence of a base such as a hydroxide such as sodium hydroxide or potassium hydroxide or a carbonate such as sodium carbonate or potassium carbonate or a hydrogen carbonate such as sodium hydrogen carbonate or potassium hydrogen carbonate can be used. Preferably potassium carbonate is used. The reaction is done in a presence of a catalyst such as CuCl or CuBr or Cu acetate preferably CuCl is used. The molar ratio between used base and the Compound (6) can be between 2:1 and 5:1, preferably it is between 2.5:1 and 3.5:1. The molar ratio between the catalyst and the Compound (6) can be between 0.15:1 and 0.4:1, preferably it is between 0.2:1 and 0.3:1. The reaction is performed under a protective gas, for example using nitrogen or argon. We have surprisingly found that when the protective gas is streamed above the reaction mixture (comparing to the state when the protecting gas constantly stays above the mixture), the reaction time can be significantly decreased. The protective atmosphere is optionally streamed above the reaction mixture, i.e. it enters in a first place the space above the reaction mixture and on another place it leaves the space above the reaction mixture by a defined rate. The rate can be between 1 and 100 l/minute (liter/minute), preferably it is between 10 and 100 l/minute, more preferably it is between 30 and 60 l/minute. Compounds (6) and (7) are mixed with the base and the catalyst in the solvent. The resulting mixture is stirred under the flow of the protective gas at a temperature between 80° C. and the reflux temperature of used solvent for between 2 and 6 hours. The reaction progress can be monitored by a suitable analytical technique, e.g. by HPLC or GC. After the reaction is finished the mixture is cooled to a temperature between −20° C. and 10° C. To the mixture water or an aqueous solution of an acid is added. The acid can be selected for example from HCl or phosphoric acid or formic acid, preferably HCl is used. The concentration of the acid in water can be between 0.1 g/ml and 0.5 g/ml, preferably it is between 0.15 g/ml and 0.25 g/ml. The volume ratio between water and the solvent used in the reaction can be between 1.8:1 and 3:1. The volume ratio between aqueous solution of the acid and the solvent used in the reaction can be between 1.5:1 and 3:1, preferably it is between 1:1.5 and 1:2. The aqueous acid or water is added slowly, for example in the course of 5 or 10 or 20 or 30 or 40 minutes. The temperature of the mixture during the addition is maintained below 22° C. The temperature of the mixture is set to between 10° C. and 25° C. and pH of the mixture is set to 2.4-2.6 using for example hydrochloric acid (HCl). The mixture is stirred for between 20 and 60 minutes to obtain a suspension. The obtained suspension is filtered off and the filtrated solid is washed with a water solution of an acid (for example with 0.01 M HCl solution) and optionally dried.

Obtained solid can be purified for example by a process comprising dissolving the solid in a mixture of an acetate and an alcohol and washing obtained mixture with a water solution of an acid. The concentration of the solid in the mixture can be between 0.05 g/ml and 0.3 g/ml, preferably it is between 0.09 g/ml and 0.15 g/ml. The acetate can be selected for example from methyl acetate or ethyl acetate or propyl acetate or butyl acetate or a mixture thereof. The alcohol can be selected for example from methanol or ethanol or propanol or 2-propanol or isopropanol or butanol or tert-butanol or a mixture thereof. The volume ration between the acetate and the alcohol can be between 8:1 and 12:1. The volume ration between the mixture of the acetate and the alcohol and the water solution of an acid can be between 1:1 and 2:1, preferably it is between 1.3:1 and 1.7:1. The phases are separated. The organic phase can be distilled off to obtain solid Compound (5) or Compound (5) can be isolated can be by using following procedure. The obtained organic phase is mixed with the solvent, preferably toluene. The volume ration between the solvent and acetate/alcohol mixture can be between 1:1 and 1:1.5. Obtained mixture can be optionally heated to a temperature between 50° C. and 80° C. to obtain a solution. In a case two phases system is formed, the phases are separated. The organic phase is concentrated to 35-45% of the original volume. The mixture is cooled to a temperature between 20° C. and 25° C. and stirred at this temperature for between 3 and 15 hours to obtain a suspension. The solid Compound (5) is filtered off and optionally dried.

In a case $R_1$ is $CH_3$, Compound (5) corresponds to the following formula:

(5)

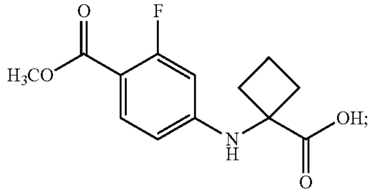

and the obtained solid form can be characterized by XRPD pattern having 2θ values 5.2°, 10.4° and 17.3° 2θ (±0.2 degrees 2θ). The solid form can be also characterized by XRPD pattern having 2θ values 5.2°, 10.4°, 17.10, 17.3° and 21.5° 2θ (±0.2 degrees 2θ). The solid form can be further characterized by XRPD pattern described in following Table:

| Angle 2-Theta° | Intensity % |
|---|---|
| 5.2 | 16.4 |
| 10.4 | 24.3 |
| 13.8 | 1.4 |
| 14.5 | 2.8 |
| 15.6 | 8.4 |
| 16.2 | 3.1 |
| 16.6 | 4.8 |
| 17.1 | 76.7 |
| 17.3 | 100.0 |
| 18.8 | 8.6 |
| 19.9 | 3.2 |
| 20.9 | 8.5 |
| 21.1 | 9.0 |
| 21.5 | 42.0 |
| 22.1 | 7.8 |
| 22.8 | 26.9 |
| 23.0 | 21.5 |
| 23.4 | 2.2 |
| 24.2 | 78.3 |
| 25.0 | 2.4 |
| 25.6 | 23.0 |
| 26.2 | 2.2 |
| 27.2 | 6.5 |
| 27.8 | 1.7 |
| 28.4 | 3.5 |
| 29.0 | 16.2 |
| 29.6 | 2.9 |
| 30.3 | 3.5 |
| 30.9 | 11.4 |
| 31.6 | 2.4 |
| 31.8 | 6.8 |
| 32.6 | 7.2 |
| 33.0 | 4.7 |
| 33.5 | 1.3 |
| 34.1 | 3.2 |
| 34.6 | 3.5 |

Figure 2:
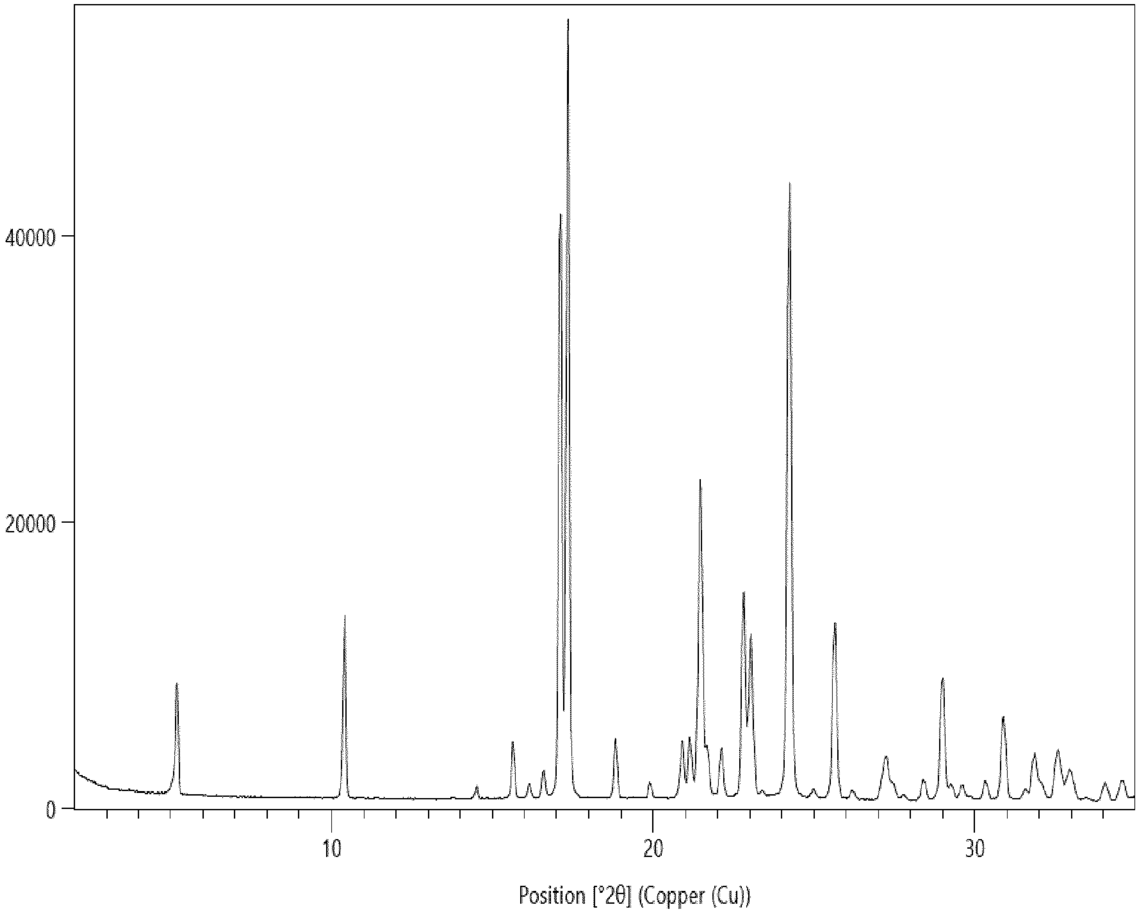
FIG. 2: XRPD pattern of solid form of 1-((3-fluoro-4-(methoxycarbonyl)phenyl-) amino)cyclobutane-1-carboxylic acid prepared according to Example 1.

The solid form can be also characterized by XRPD pattern depicted in FIG. 2.

The presented invention also relates to solid form of Apalutamide 2-propanol solvate, Form 7, characterized by XRPD pattern having 2θ values 4.6°, 7.1°, 13.8° and 16.0° 2θ (±0.2 degrees 2θ). The Form 7 can be further characterized by XRPD pattern having 2θ values 4.6°, 7.1°, 10.7°, 13.8°, 16.0°, 18.5° and 20.1° 2θ (±0.2 degrees 2θ). The Form 7 can be further characterized by XRPD 2θ values (±0.2 degrees 2θ) stated in following table:

| Angle (2θ) | Intensity (%) |
|---|---|
| 4.6 | 94.1 |
| 7.1 | 67.7 |
| 9.2 | 9.9 |
| 10.7 | 19.2 |
| 11.7 | 4.9 |
| 13.0 | 5.3 |
| 13.8 | 38.2 |
| 14.2 | 4.7 |
| 14.9 | 3.5 |
| 16.0 | 100.0 |
| 16.8 | 22.0 |
| 18.5 | 24.7 |
| 19.2 | 3.2 |
| 20.1 | 38.1 |
| 20.6 | 16.8 |
| 21.4 | 8.7 |
| 21.7 | 8.8 |
| 22.2 | 19.8 |
| 22.6 | 12.8 |

-continued

| Angle (2θ) | Intensity (%) |
|---|---|
| 22.8 | 6.4 |
| 23.6 | 4.1 |
| 23.8 | 7.3 |
| 24.2 | 12.3 |
| 24.8 | 19.6 |
| 25.2 | 10.5 |
| 25.7 | 6.8 |
| 26.5 | 28.9 |
| 27.5 | 7.4 |
| 27.9 | 4.2 |
| 28.5 | 4.0 |
| 29.3 | 2.4 |
| 30.1 | 8.9 |
| 30.6 | 5.3 |
| 31.2 | 4.8 |
| 32.1 | 6.6 |
| 32.8 | 4.5 |
| 34.1 | 3.3 |
| 34.4 | 3.5 |

Figure 13:
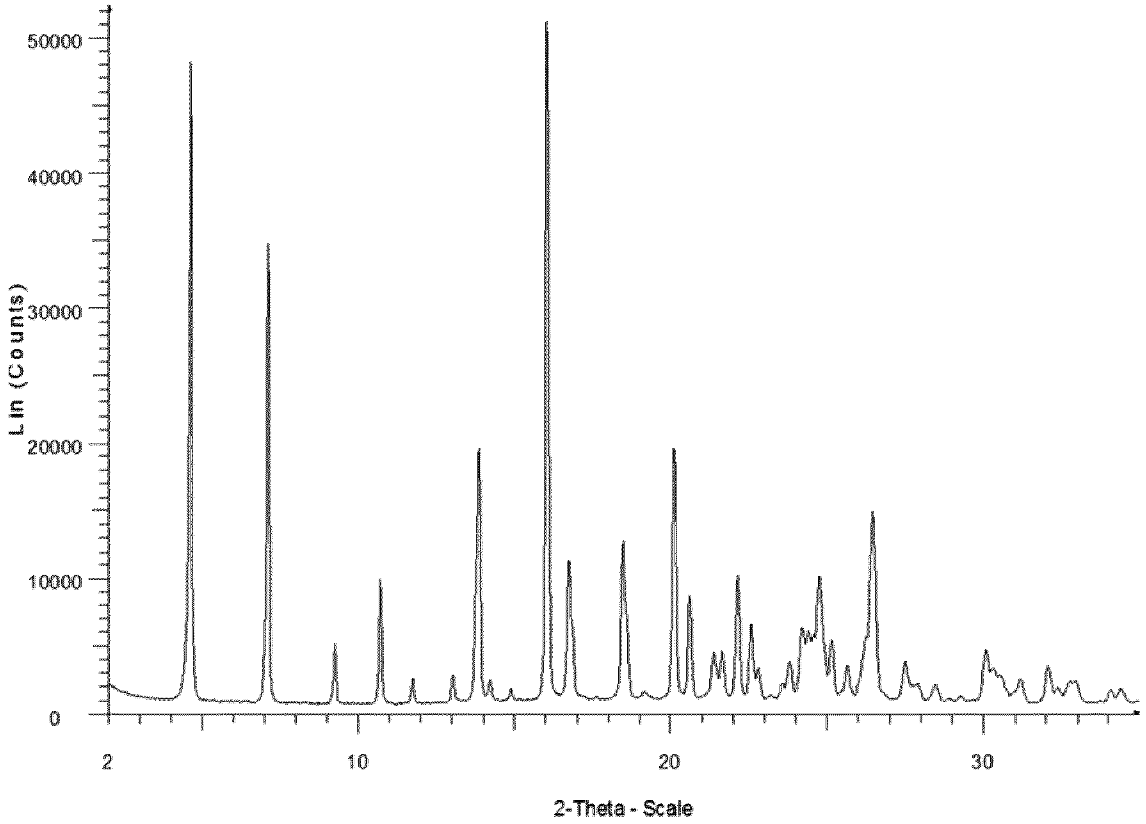
FIG. 13: XRPD pattern of solid Form 7 of Apalutamide 2-propanol solvate prepared according to Example 9 or Example 10.
Figure 14:
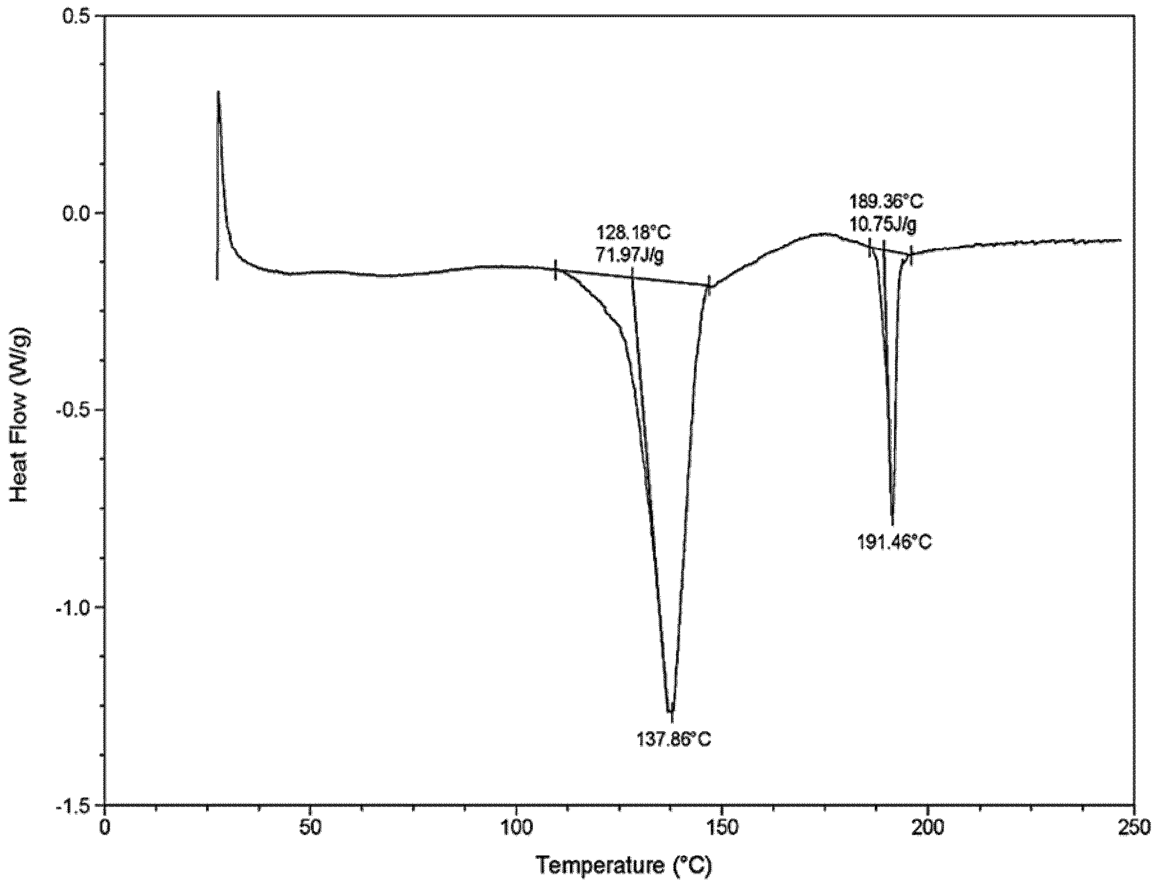
FIG. 14: DSC pattern of solid Form 7 of Apalutamide 2-propanol solvate prepared according to Example 9 or Example 10.
Figure 15:
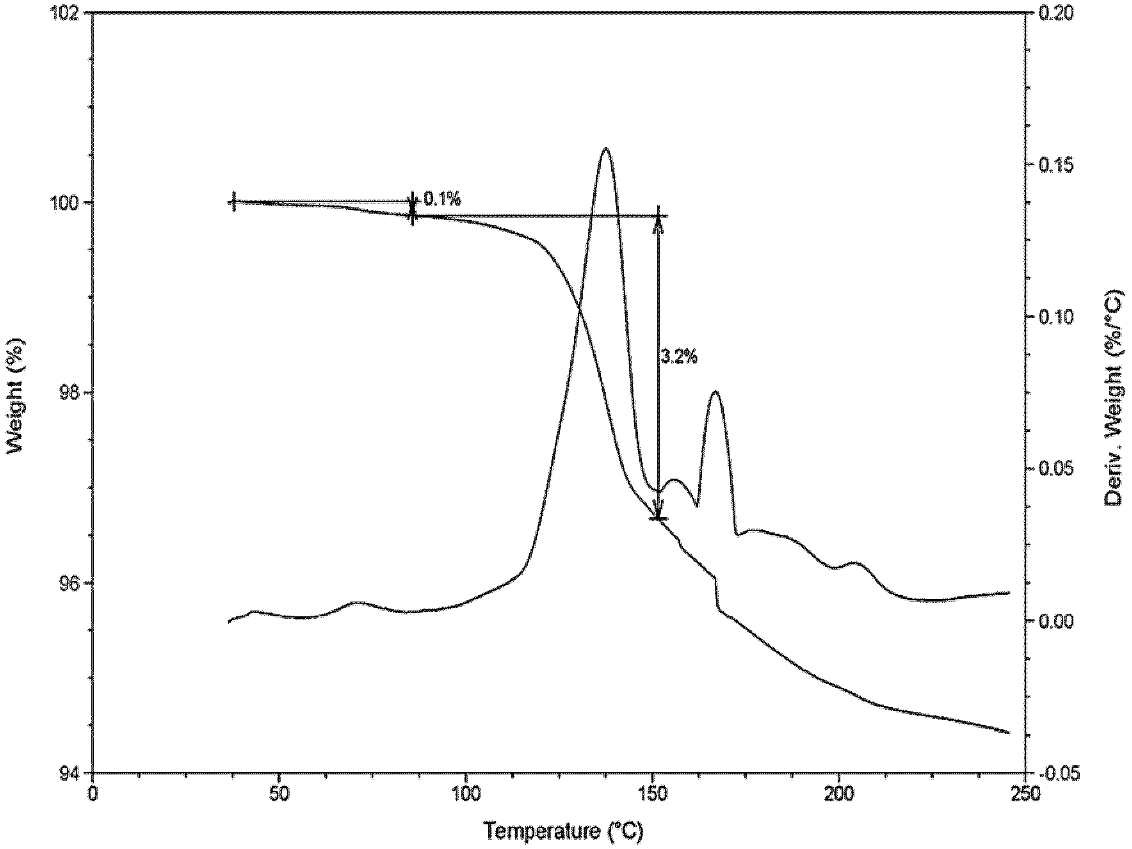
FIG. 15: TGA pattern of solid Form 7 of Apalutamide 2-propanol solvate prepared according to Example 9 or Example 10.
Figure 17:
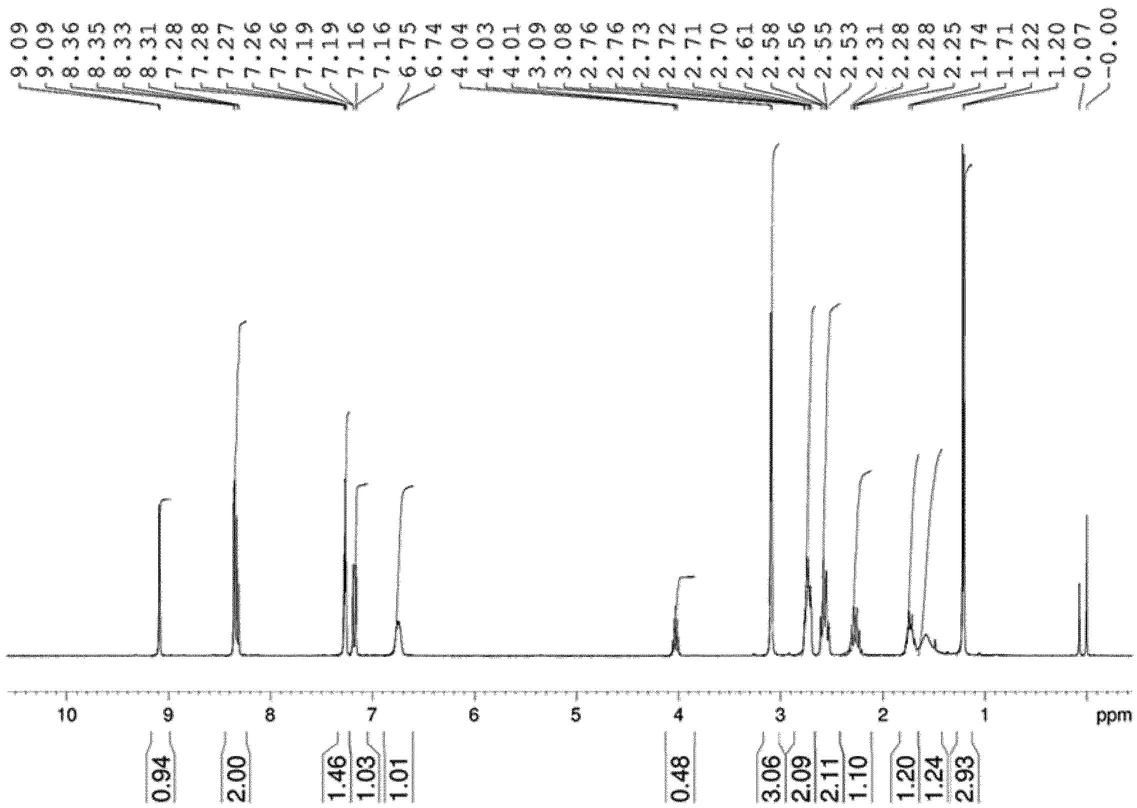
FIG. 17: NMR pattern of solid Form 7 of Apalutamide 2-propanol solvate prepared according to Example 9 or Example 10.

The Form 7 can be also characterized by XRPD pattern depicted in FIG. 13 or DSC pattern depicted in FIG. 14 or TGA pattern depicted in FIG. 15 or NMR pattern depicted in FIG. 17.

The Form 7 can be prepared by a process comprising:

a. Dissolving Apalutamide in 2-propanol;

b. Isolating the solid form.

The concentration of Apalutamide in 2-propanol can be between 0.04 g/ml and 0.06 g/ml. Apalutamide can be optionally dissolved at a temperature between 60° C. and 75° C. The mixture of Apalutamide and 2-propanol, optionally heated to 60° C.-75° C. can be stirred for between 30 and 120 minutes to dissolve Apalutamide. The mixture is then cooled to a temperature between 15° C. and 25° C. and stirred at this temperature for between 5 and 15 hours. The solid mass is filtered off and optionally dried, for example on air for between 2 and 10 hours, to provide Apalutamide 2-propanol solvate, Form 7.

The Form 7 can be also prepared by a process comprising:

a. Mixing Apalutamide with 2-propanol to prepare a slurry (mixture of solid Apalutamide in the solvent);

b. Isolating the solid form.

The concentration of Apalutamide in 2-propanol can be between 0.04 g/ml and 0.06 g/ml. Apalutamide is mixed with 2-propanol, preferably at a temperature between 15° C. and 25° C. The mixture is stirred for between 10 and 20 hours. The solid mass is filtered off and optionally dried, for example on air for between 2 and 10 hours, to provide Apalutamide 2-propanol solvate, Form 7.

Form 7 can be also prepared by a process comprising:

a. Dissolving Compound (1) with a mixture of 2-propanol and methanol, wherein the weight ratio between 2-propanol and methanol can be between 1:0.4 and 1:0.8;

b. Optionally cooling the mixture;

c. Isolating Form 7 of Compound (1).

Concentration of Compound (1) in the mixture 2-propanol and methanol can be between 0.06 g/ml and 0.1 g/ml, preferably it is between 0.075 g/ml and 0.085 g/ml. Compound (1) can be dissolved at an elevated temperature, preferably at reflux temperature of the solvent mixture. After dissolving the mixture is optionally cooled, preferably to a temperature between −10° C. and 45° C., more preferably between −10° C. and 25° C. In a most preferred embodiment of the invention, the mixture is cooled to a temperature between −10° C. and 0° C. The mixture is cooled preferably in the course of between 1 and 5 hours. The mixture is then stirred at this temperature for between 20 and 45 minutes. The solid mass is filtered off and optionally washed with cold 2-propanol and dried to obtain Compound (1) in solid Form 7.

The presented invention further relates to a solid form of Apalutamide 1-methoxy-2-propanol solvate, Form 5, characterized by XRPD pattern having 2θ values 4.70, 7.10 and 13.9° 2θ (±0.2 degrees 2θ). The Form 5 can be further characterized by XRPD pattern having 2θ values 4.7°, 7.1°, 93°, 10.7°, 13.9° and 16.0° 2θ (±0.2 degrees 2θ). The Form 5 can be further characterized by XRPD 2θ values (±0.2 degrees 2θ) stated in following table:

| Angle (2θ) | Intensity (%) |
|---|---|
| 4.7 | 90.7 |
| 7.1 | 26.9 |
| 9.3 | 22.6 |
| 10.7 | 19.5 |
| 13.9 | 100.0 |
| 14.9 | 7.8 |
| 16.0 | 21.5 |
| 16.6 | 10.3 |
| 18.4 | 21.5 |
| 18.5 | 21.7 |
| 19.2 | 4.0 |
| 19.9 | 15.3 |
| 20.4 | 7.0 |
| 21.2 | 8.8 |
| 21.8 | 11.1 |
| 22.5 | 11.6 |
| 22.8 | 6.0 |
| 23.2 | 3.9 |
| 23.8 | 9.7 |
| 24.2 | 12.0 |
| 24.4 | 14.9 |
| 24.8 | 10.1 |
| 26.1 | 14.6 |
| 26.8 | 5.0 |
| 27.5 | 3.9 |
| 27.9 | 4.5 |
| 28.3 | 8.1 |
| 29.7 | 4.0 |
| 29.9 | 6.5 |
| 30.1 | 4.5 |
| 30.7 | 5.3 |
| 31.9 | 3.6 |
| 32.5 | 4.5 |
| 34.2 | 4.7 |
| 34.7 | 3.4 |

Figure 7:
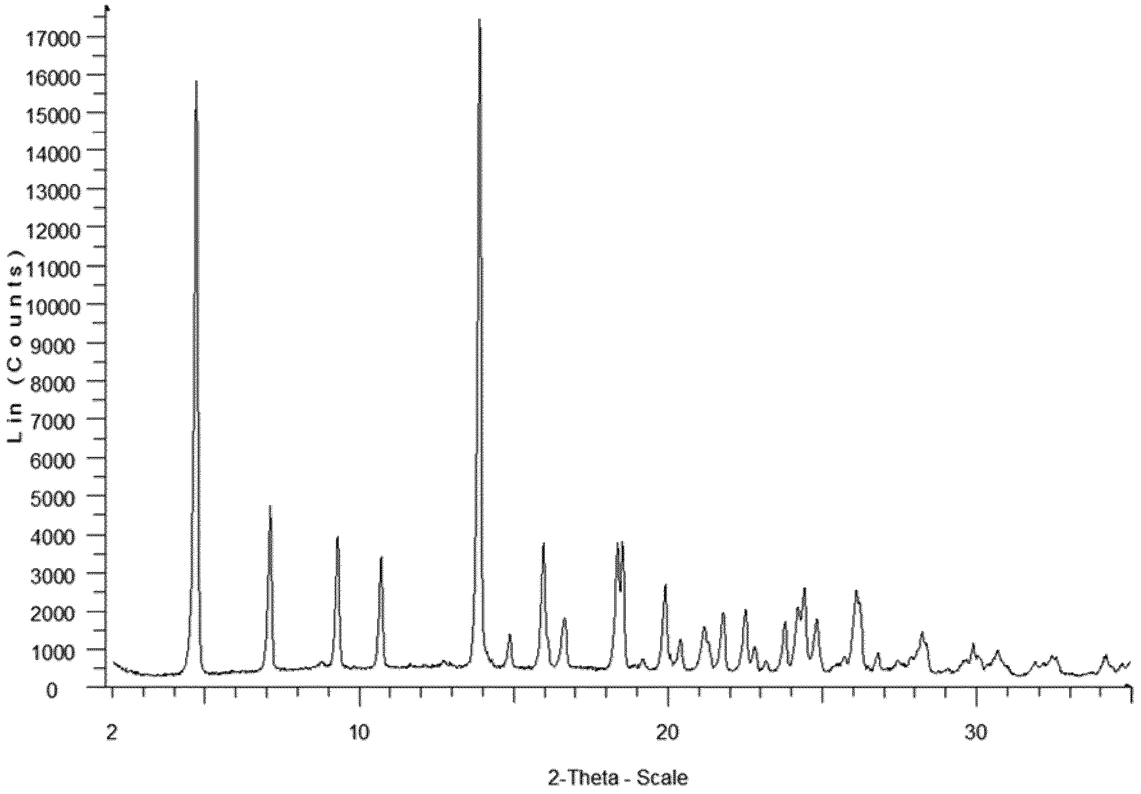
FIG. 7: XRPD pattern of solid Form 5 of Apalutamide 1-methoxy-2-propanol solvate prepared according to Example 7.
Figure 8:
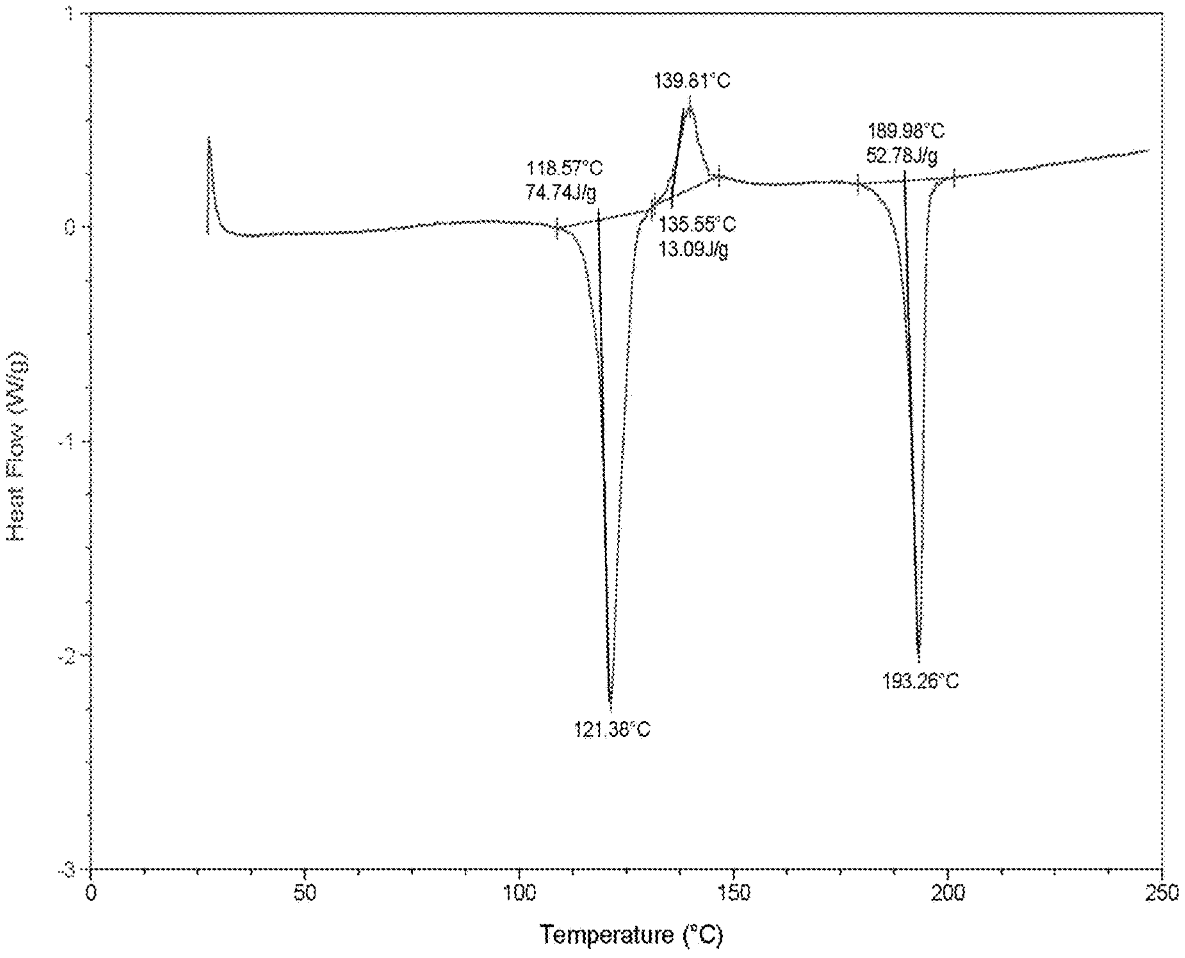
FIG. 8: DSC pattern of solid Form 5 of Apalutamide 1-methoxy-2-propanol solvate prepared according to Example 7.
Figure 9:
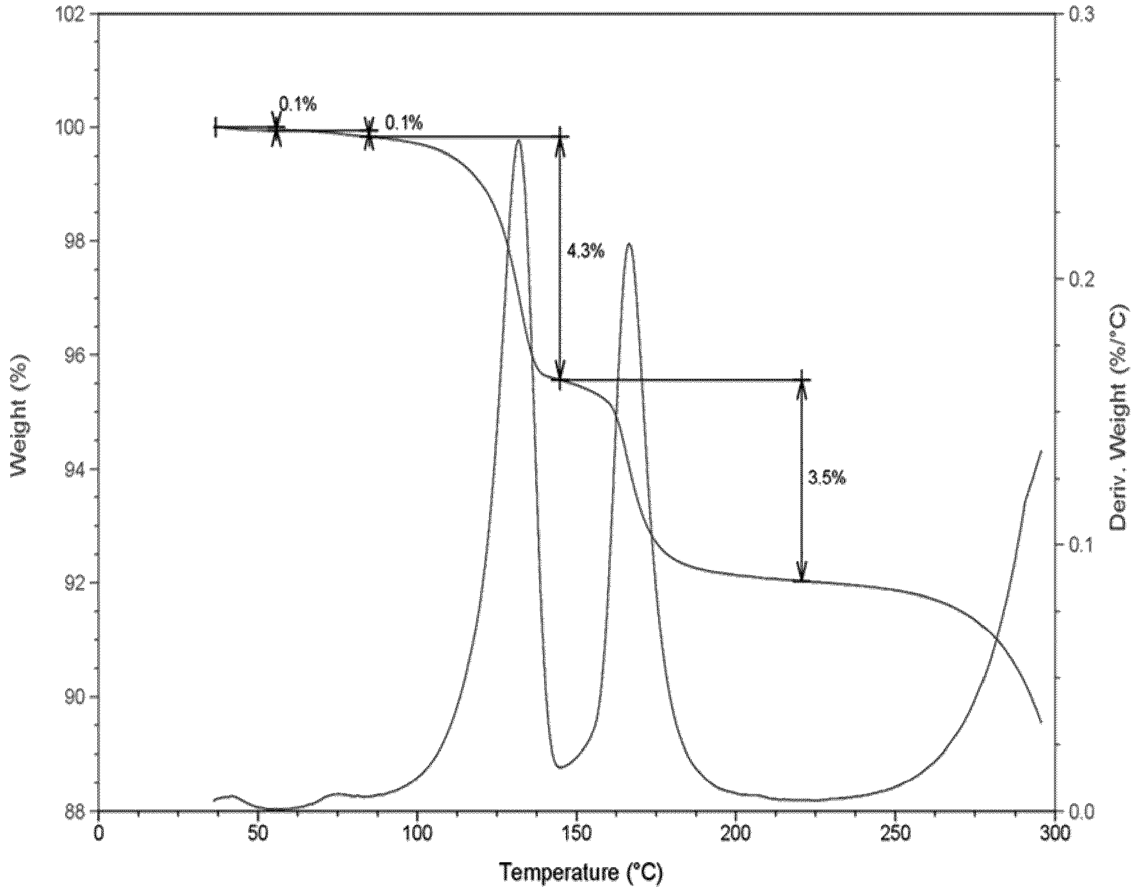
FIG. 9: TGA pattern of solid Form 5 of Apalutamide 1-methoxy-2-propanol solvate prepared according to Example 7.
Figure 16:
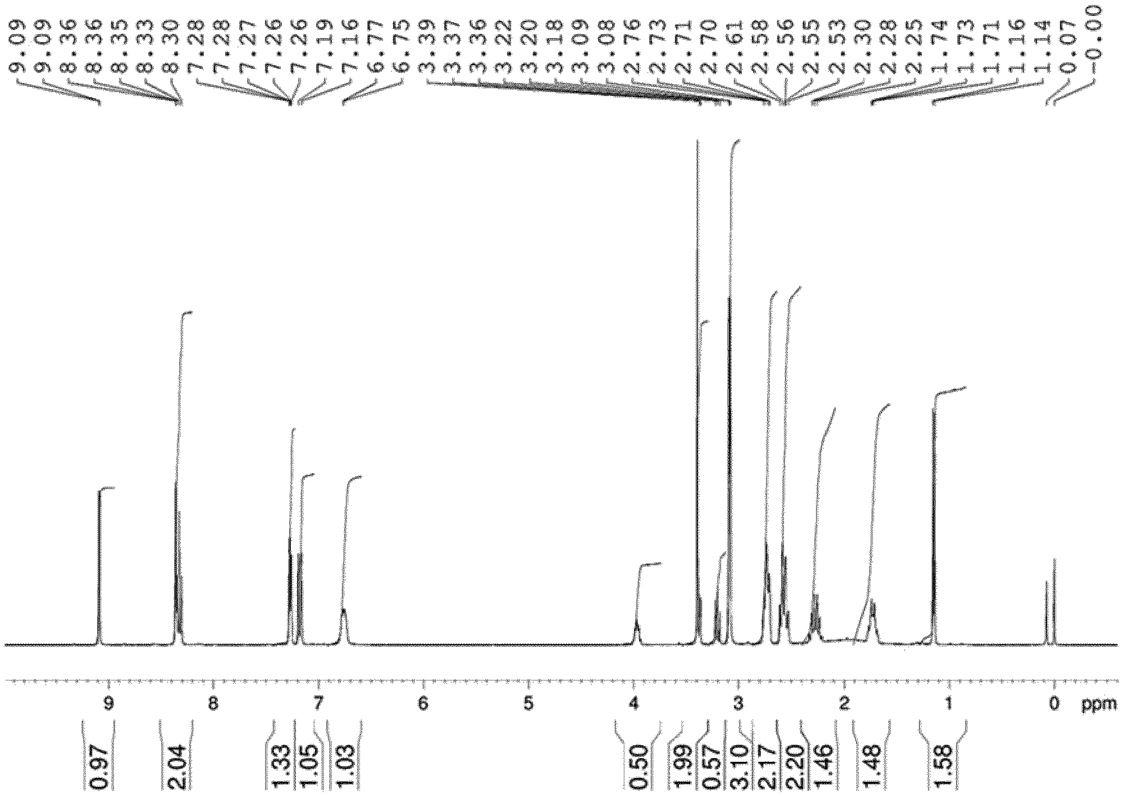
FIG. 16: NMR pattern of solid Form 5 of Apalutamide 1-methoxy-2-propanol solvate prepared according to Example 7.

The Form 5 can be also characterized by XRPD pattern depicted in FIG. 7 or DSC pattern depicted in FIG. 8 or TGA pattern depicted in FIG. 9 or NMR pattern depicted in FIG. 16.

The solid Form 5 can be prepared by a process comprising:

1. Contacting amorphous Apalutamide with 1-methoxy-2-propanol;
2. Isolating the solid form.

The concentration of Apalutamide in 1-methoxy-2-propanol can be between 0.08 g/ml and 0.15 g/ml. The mixture is stirred at a temperature between 200 and 30° C. for between 2 and 6 hours. The solid mass is filtered off and optionally dried to provide Apalutamide 1-methoxy-2-propanol solvate, Form 5.

The presented invention also relates to a solid form of Apalutamide, Form 3, characterized by:

a. XRPD pattern having 2θ values 4.7°, 7.10, 13.3°, 13.8° and 14.2° 2θ (±0.2 degrees 2θ); and
b. DSC pattern with an endotherm having an onset temperature at about 111.9°-115.9° C. and a peak at about 118.6° C.-120.3° C.

The Form 3 can be also characterized by:

a. XRPD pattern having 2θ values 4.7°, 7.10, 9.4°, 10.8°, 13.3°, 13.8°, 14.2° and 16.2° 2θ (±0.2 degrees 2θ); and
b. DSC pattern having a first peak with an endotherm having an onset temperature at about 71.2°-87.5° C. and a peak at about 78.7° C.-90.5° C. and a second peak having an onset temperature at about 111.9°-115.9° C. and a peak at about 118.6° C.-120.3° C.

The Form 3 can be further characterized by XRPD 2θ values (±0.2 degrees 2θ) stated in following table:

| Angle (2θ) | Intensity (%) |
|---|---|
| 4.7 | 100.0 |
| 7.1 | 34.1 |
| 9.4 | 4.8 |
| 10.8 | 7.9 |
| 11.6 | 3.8 |
| 13.3 | 13.6 |
| 13.8 | 17.4 |
| 14.2 | 26.3 |
| 15.1 | 6.5 |
| 16.2 | 19.0 |
| 16.7 | 19.7 |
| 17.1 | 14.3 |
| 18.3 | 20.6 |
| 20.2 | 16.8 |
| 20.5 | 6.8 |
| 21.4 | 14.5 |
| 21.9 | 7.3 |
| 22.5 | 10.0 |
| 23.4 | 5.5 |
| 24.3 | 8.8 |
| 24.7 | 10.6 |
| 25.0 | 11.4 |
| 26.1 | 12.6 |
| 26.8 | 8.2 |
| 27.9 | 6.0 |
| 30.1 | 7.2 |
| 30.4 | 6.7 |
| 31.4 | 4.2 |
| 32.8 | 4.9 |

Figure 4:
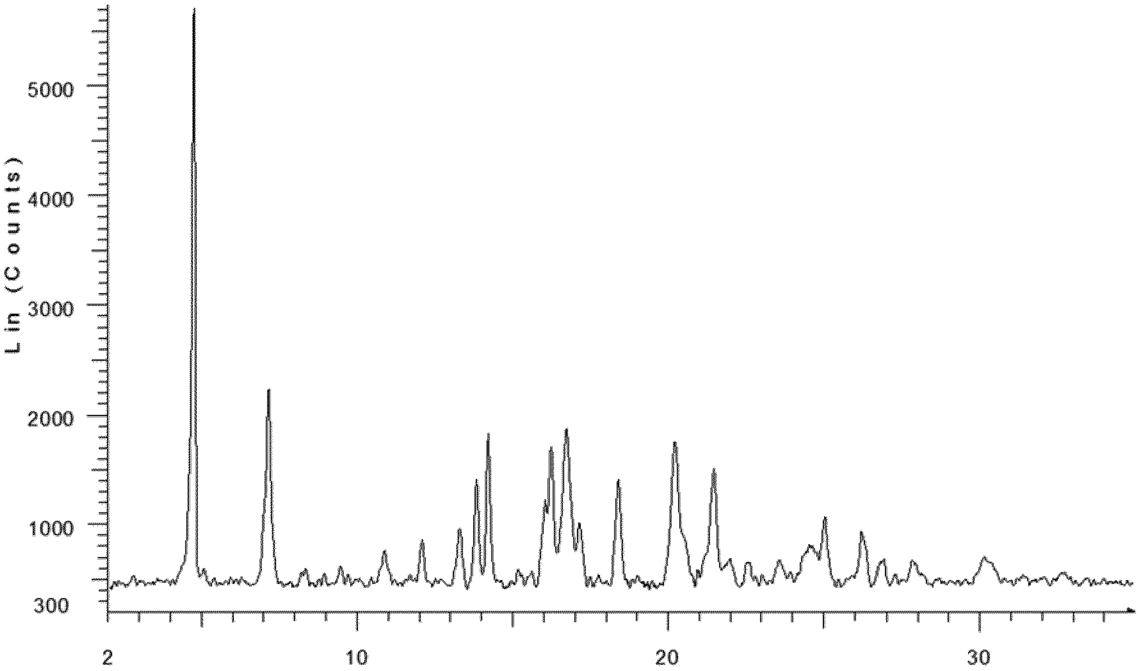
FIG. 4: XRPD pattern of solid Form 3 of Apalutamide prepared according to Example 5 or Example 6.
Figure 5:
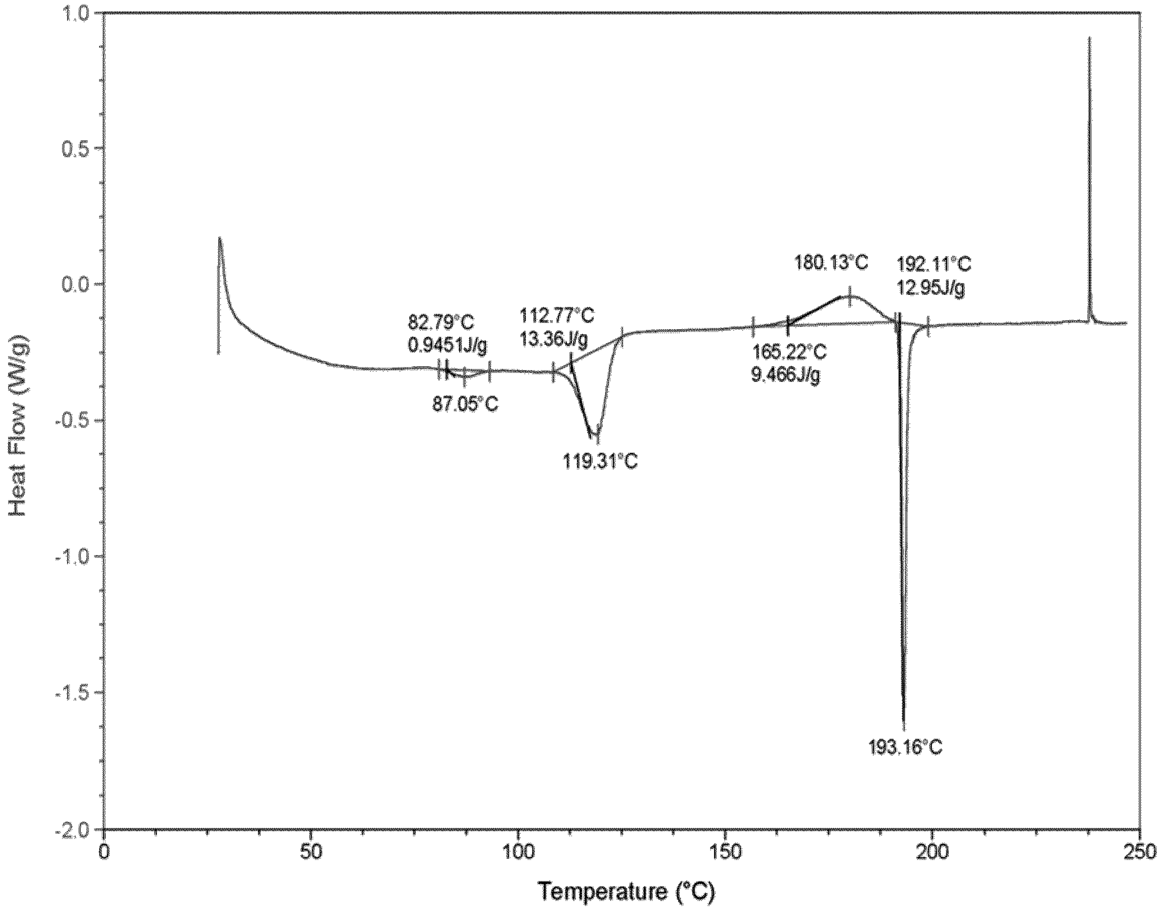
FIG. 5: DSC pattern of solid Form 3 of Apalutamide prepared according to Example 5 or Example 6.
Figure 6:
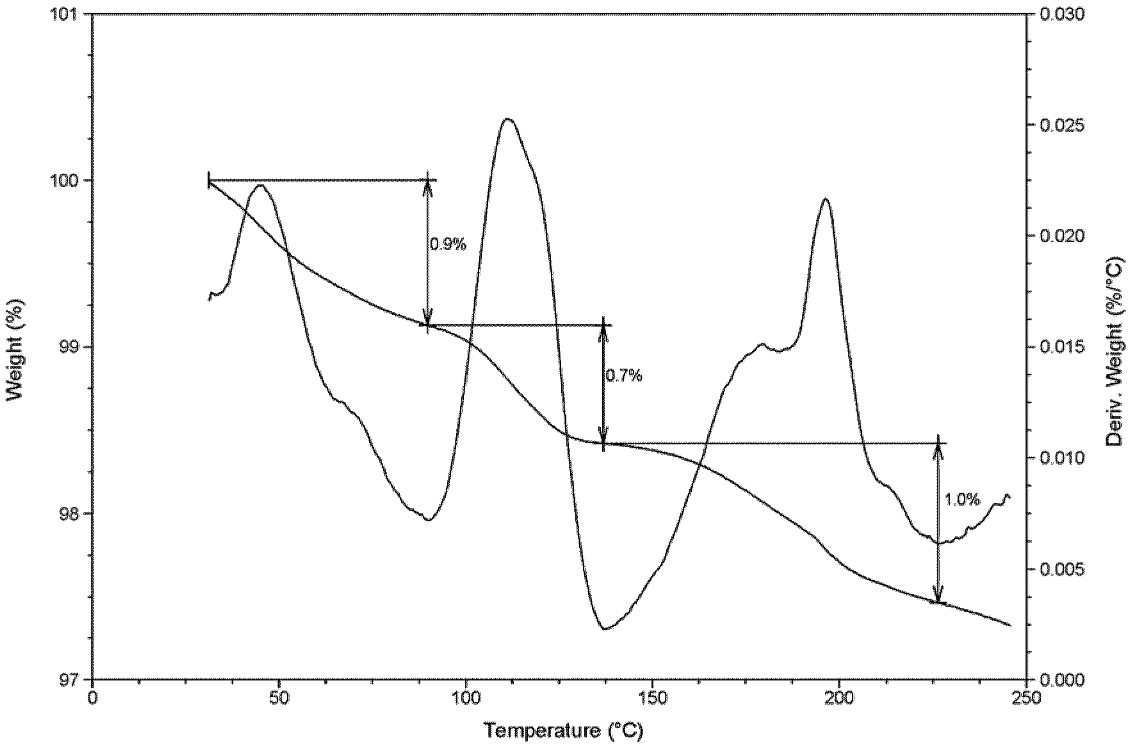
FIG. 6: TGA pattern of solid Form 3 of Apalutamide prepared according to Example 5 or Example 6.

The Form 3 can be also characterized by XRPD pattern depicted in FIG. 4 or DSC pattern depicted in FIG. 5 or TGA pattern depicted in FIG. 6.

The Form 3 can be prepared by a process comprising:

a. Mixing amorphous Apalutamide with water to prepare a slurry (mixture of solid Apalutamide and water);
b. Isolating the solid form.

The concentration of Apalutamide in water can be between 0.08 g/ml and 0.15 g/ml. The mixture is stirred at a temperature between 15° C. and 30° C. for between 1 and 5 hours. The solid mass is filtered off and optionally dries to provide the solid Form 3.

The solid Form 3 can be also obtained by exposing Apalutamide crystalline Form 7 or Form 5 to a temperature between 40° C. and 60° C. and humidity between 75% of relative humidity and 90% of relative humidity for between 30 and 40 days.

Form 3 was tested at high humidity (75% RH/40° C.) for 6 months or at 90% RH/55° C.) for 1 month. There was no change in XRPD pattern after the test. Form 3 is therefore very stable at this conditions. When prior art Form A (disclosed in WO2013184681A1) was tested at the same conditions, the crystalline structure changed during the test.

The presented invention also relates to a solid form of Apalutamide methyl isobutyl ketone solvate, Form 6, characterized by XRPD pattern having 2θ values 3.8°, 6.9°, 8.8°, 16.2° and 20.8° 2θ (±0.2 degrees 2θ). The Form 6 can be further characterized by XRPD pattern having 2θ values 3.8°, 6.9°, 7.7°, 8.8°, 15.4°, 16.2° and 20.8° 2θ (±0.2 degrees 2θ).

The Form 6 can be further characterized by XRPD 2θ values (±0.2 degrees 2θ) stated in following table:

| Angle (2θ) | Intensity (%) |
|---|---|
| 3.8 | 32.2 |
| 6.9 | 100.0 |
| 7.7 | 28.2 |
| 8.3 | 5.7 |
| 8.8 | 24.3 |
| 10.1 | 3.8 |
| 11.6 | 9.0 |
| 11.7 | 14.7 |
| 12.3 | 3.0 |
| 12.6 | 12.4 |
| 13.6 | 8.8 |
| 14.2 | 5.7 |
| 14.4 | 6.9 |
| 14.8 | 5.2 |
| 15.1 | 13.1 |
| 15.4 | 22.8 |
| 15.6 | 9.0 |
| 16.2 | 59.6 |
| 16.7 | 14.1 |
| 16.8 | 8.1 |
| 17.1 | 15.6 |
| 17.4 | 14.0 |
| 17.7 | 6.7 |
| 18.2 | 5.8 |
| 19.1 | 13.3 |
| 19.7 | 5.2 |
| 19.9 | 14.0 |
| 20.2 | 7.5 |
| 20.3 | 8.8 |
| 20.8 | 31.7 |
| 21.1 | 15.5 |
| 21.3 | 10.1 |
| 21.9 | 9.3 |
| 22.3 | 4.9 |
| 22.6 | 10.1 |
| 23.1 | 6.0 |
| 23.3 | 10.3 |
| 23.8 | 11.3 |
| 24.1 | 6.3 |
| 24.6 | 12.8 |
| 25.0 | 7.4 |
| 25.4 | 9.2 |
| 25.5 | 9.0 |
| 25.9 | 6.3 |
| 26.2 | 4.4 |
| 26.7 | 6.6 |
| 26.9 | 5.3 |
| 27.7 | 5.2 |
| 28.2 | 7.1 |
| 28.7 | 4.8 |
| 29.2 | 4.5 |
| 30.4 | 3.7 |
| 31.7 | 4.0 |

Figure 10:
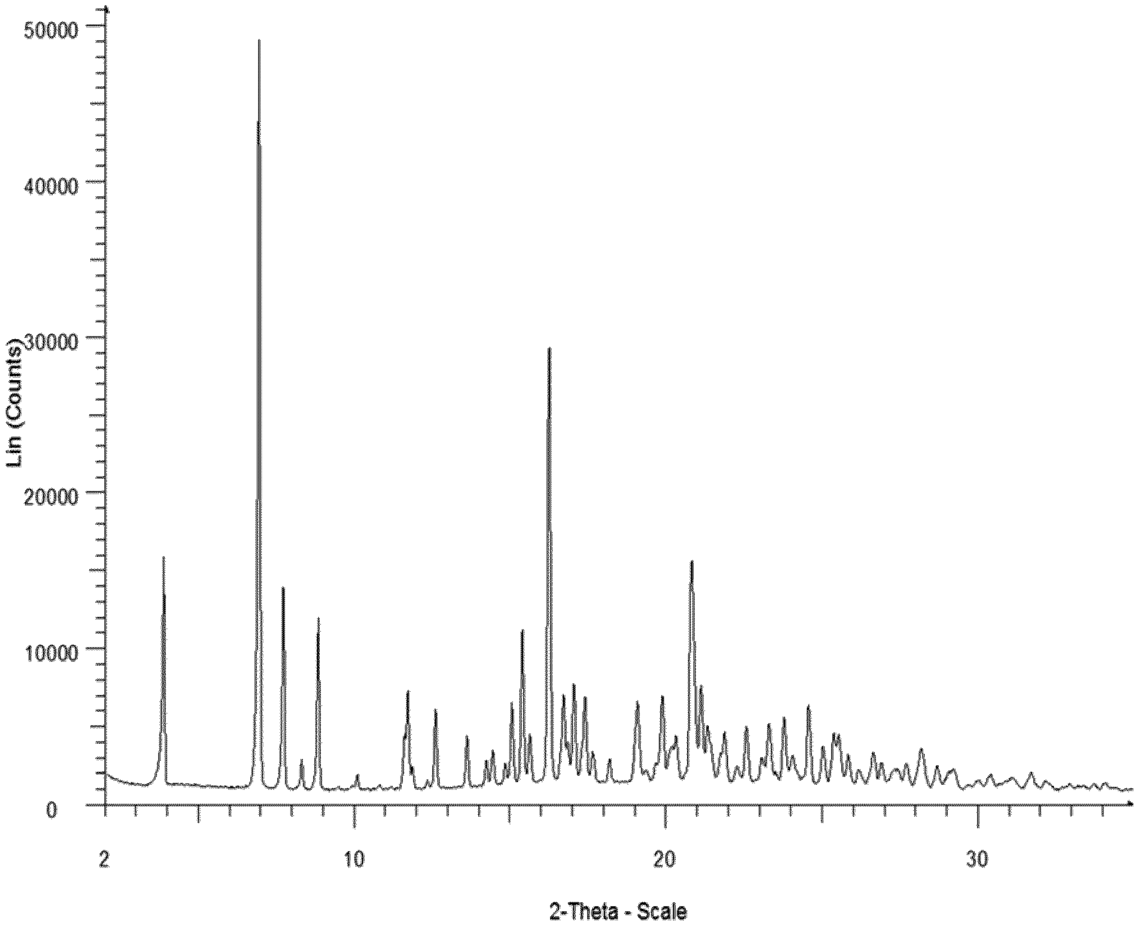
FIG. 10: XRPD pattern of solid Form 6 of Apalutamide methyl isobutyl ketone solvate prepared according to Example 8.
Figure 11:
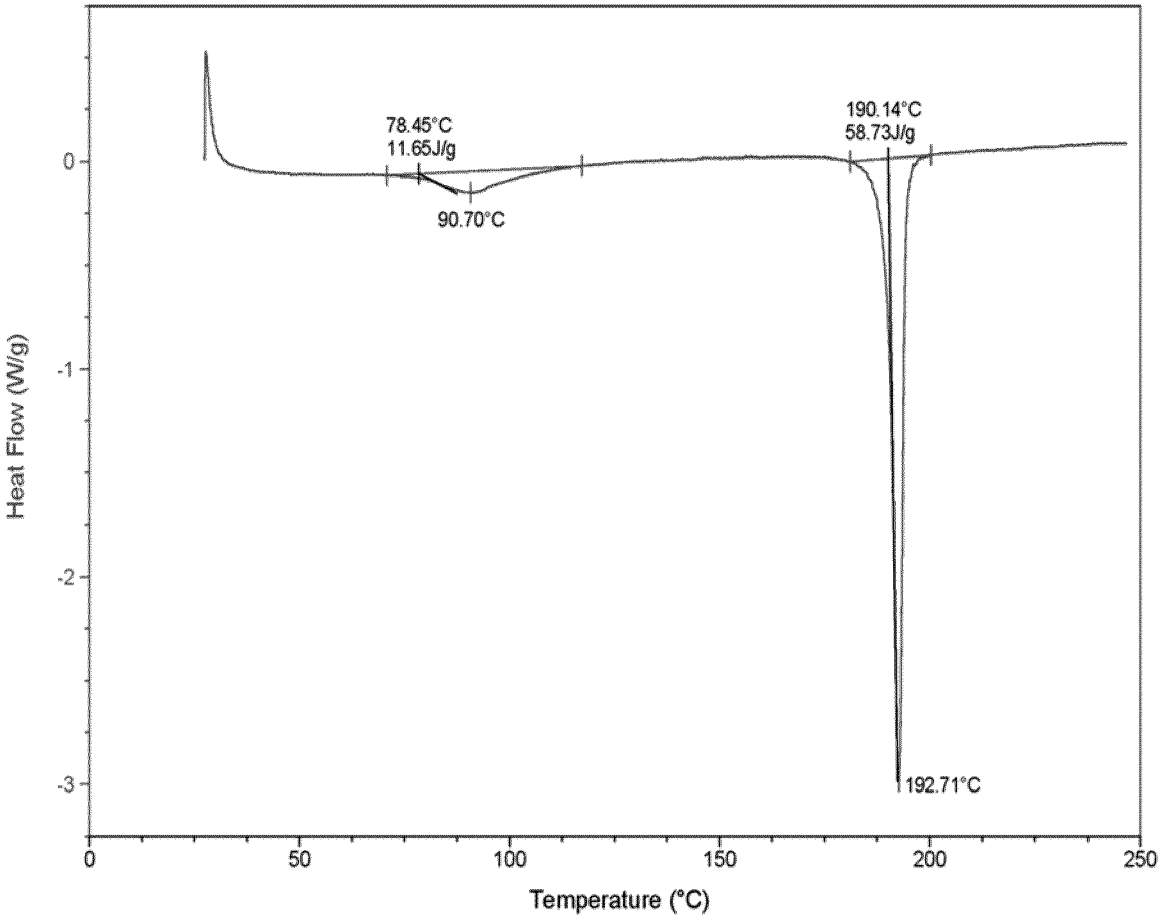
FIG. 11: DSC pattern of solid Form 6 of Apalutamide methyl isobutyl ketone solvate prepared according to Example 8.
Figure 12:
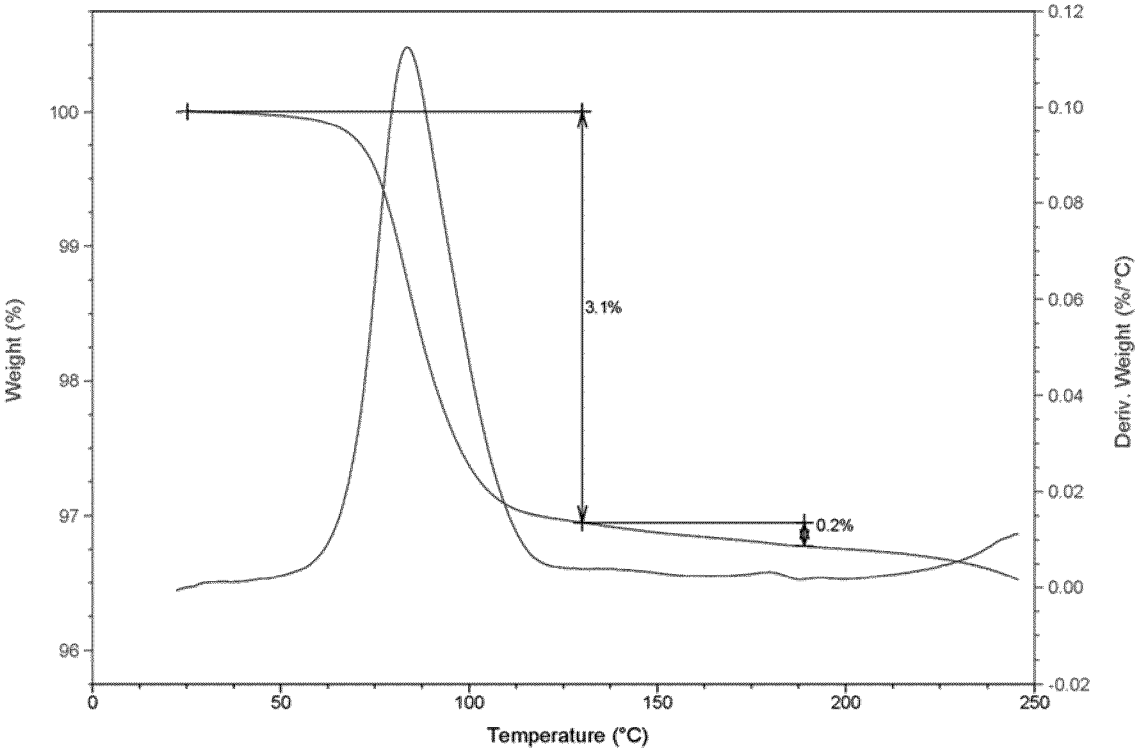
FIG. 12: TGA pattern of solid Form 6 of Apalutamide methyl isobutyl ketone solvate prepared according to Example 8.

The Form 6 can be also characterized by XRPD pattern depicted in FIG. 10 or DSC pattern depicted in FIG. 11 or TGA pattern depicted in FIG. 12.

The Form 6 can be prepared by a process comprising:

1. Contacting amorphous Apalutamide with methyl isobutyl ketone;
2. Isolating the solid form.

The concentration of Apalutamide in methyl isobutyl ketone can be between 0.14 mg/g and 0.18 mg/g. The mixture is heated to a temperature between 55° C. and 70° C. and stirred at this temperature for between 120 minutes. The mixture is then cooled to a temperature between 20° C. and 30° C. and stirred at this temperature for between 5 and 12 hours. The solid mass is filtered off and optionally dried to provide the solid Form 6.

The invention will be further illustrated by the following examples.

EXAMPLES

Example 1: Preparation of Compound of Formula (5) ($R_1$: $CH_3$), 1-((3-fluoro-4-(methoxycarbonyl) phenyl)amino)cyclobutane-1-carboxylic Acid

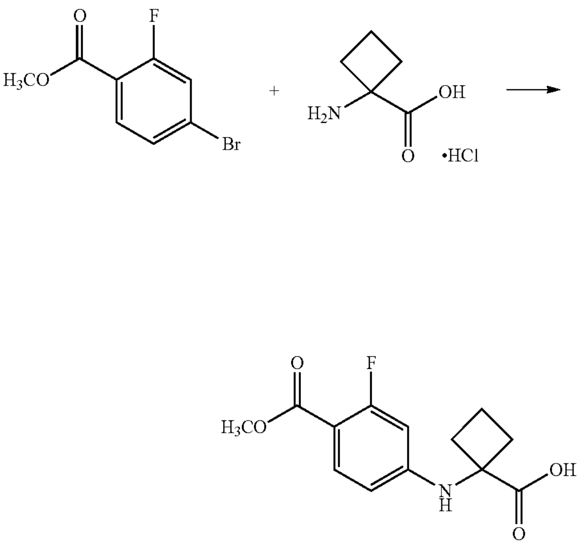

20 g of methyl 4-bromo-2-fluorobenzoate were mixed with 19.51 g of 1-amino-cyclobutane-1-carboxylic acid hydrochloride salt, 35.6 g of potassium carbonate, 2.124 g of Copper (I) chloride and 120 ml of dimethylformamide (DMF). The resulting mixture was stirred under significant flow of argon (10 l/minute) and was heated to 100-110° C. The mixture was stirred for 4 hours.

Then, the mixture was allowed to cool down to 20-25° C. and then to 0° C.-5° C. To the mixture 240 ml of water was added in the course of 2 minutes. The mixture was cooled to 10-15° C. Concentrated (35%) aqueous HCl was added to adjust pH to 2.5. The formed solid was collected by filtration, washed with 50 ml of 0.01 M aqueous HCl and suction dried for 20 minutes. Obtained solid was dissolved in a mixture comprising 250 ml of ethyl acetate and 25 ml of methanol. The mixture was washed with 200 ml of 0.01 M aqueous HCl. The phases were separated. To the organic phase 250 ml of toluene was added. The mixture was heated to 60° C. Two-phases system appeared. The phases were separated and the organic phase was concentrated (60° C., 300→200 mbar) to amount 200 g to obtain a suspension.

The hot suspension was allowed to cool down to 20-25° C. and was stirred overnight. The solid was filtrated and washed with 50 ml of toluene and dried (45° C., 100 torr, $N_2$ strip, 4 hours). 17.1 g (74% yield of the theoretical yield) of 1-((3-fluoro-4-(methoxycarbonyl-) phenyl)amino)cyclobutane-1-carboxylic acid in purity 99.67% (HPLC IN, 277 nm) was obtained.

XRPD of obtained solid corresponds to XRPD pattern depicted in FIG. 2.

Example 2: Preparation of Compound of Formula (2) (R1: CH3, R2:CH3), methyl 2-fluoro-4-((1-(methoxycarbonyl)cyclobutyl)amino)benzoate

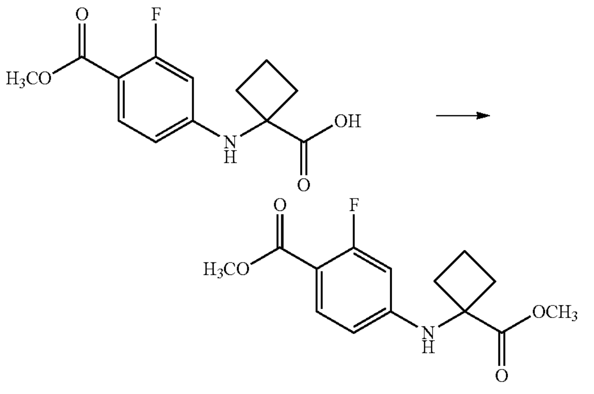

10.4 g of 1-((3-fluoro-4-(methoxycarbonyl)phenyl) amino)cyclobutane-1-carboxylic acid was suspended in 66 ml of methanol. 2.161 ml of concentrated sulfuric acid (96%) was added drop-wise.

Then, the mixture was heated to reflux and stirred for 4 hrs. The mixture was allowed to cool down to 20° C.-25° C. A solution of 4.12 g of sodium carbonate in 66 ml of water was added slowly in the course of 10 minutes to keep $C_{02}$ evolution mild. The mixture was then stirred at 20° C.-25° C. for 1 hr. Obtained solid was collected by filtration and washed with 30 ml of water and dried (45° C., 100 torr, $N_2$ strip, 16 hrs). 10.6 g (96% of the theoretical yield) of methyl 2-fluoro-4-((1-(methoxycarbonyl)cyclobutyl)amino)benzoate was obtained in 99.26% purity (HPLC in, 277 nm).

XRPD pattern of obtained solid corresponds to XRPD pattern depicted in FIG. 3.

Example 3: Preparation of Compound of Formula (4) (R1: CH3), methyl 4-(7-(6-cyano-5-(trifluoromethyl)pyridin-3-yl)-8-oxo-6-thioxo-5,7-diazaspiro [3.4]octan-5-yl)-2-fluorobenzoate

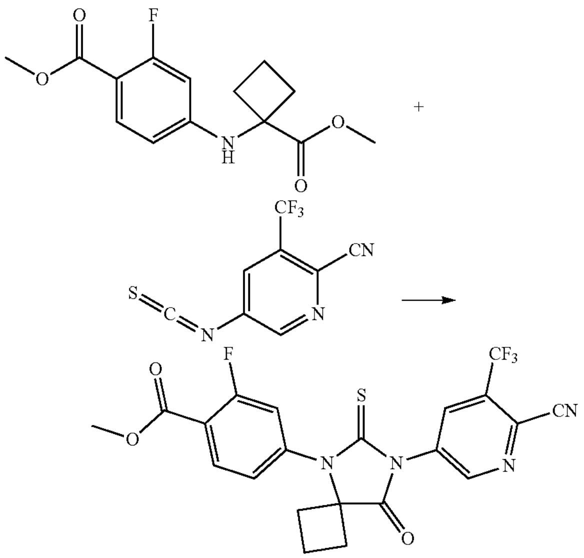

10 g of methyl 2-fluoro-4-((1-(methoxycarbonyl)cyclobutyl)amino)benzoate was mixed with 50 ml of tetrahydrofurane (THF). The mixture was cooled down to 8-12° C. 26.1 ml of lithium bis(trimethylsilyl)amide (LiHMDS) (1.5 M solution in THF) was added drop-wise. while the temperature was kept at 8-12° C. The mixture was stirred at 8-12° C. for 5 minutes and a solution of 8.96 g of 5-isothiocyanato-3-(trifluoromethyl)picolinonitrile in 15 ml of THF was added drop-wise while the temperature was kept at 8-12° C. After addition, the mixture was cooled to 0-5° C. and was stirred for 30 minutes. The mixture was diluted with 50 ml of methyl tert-buty ether. It was cooled to 0-5° C. again and 50 ml of 1M aqueous HCl was added so the temperature does not exceed 20° C.

The phases were separated and the organic phase was washed twice with 50 ml of 1M aqueous HCl. To the organic phase 500 mg of active carbon was added. The mixture was stirred for 30 minutes. The mixture was filtered and the filtrate was mixed with 100 ml of 2-propanol. The mixture was concentrated (70° C., 400 mbar) to amount 80 g. The mixture was allowed to cool down to RT with stirring (700 rpm) to obtain a suspension. The mixture was stirred for 1 hour at 20-25° C. The solid was collected by filtration, washed twice with 15 ml of cold (<10° C.) 2-propanol, suction dried for 20 min and then dried (20-25° C., 100 torr, $N_2$ strip, over weekend; then 80° C., 100 torr, $N_2$ strip), 13.85 g of methyl 4-(7-(6-cyano-5-(trifluoromethyl)pyridin-3-yl)-8-oxo-6-thioxo-5,7-diazaspiro[3.4]octan-5-yl)-2-fluorobenzoate (81% of theoretical yield), 99.21% purity (HPLC in, 275 nm) was obtained.

The obtained solid material was dissolved in 140 ml of 2-propanol at reflux with stirring. The mixture was allowed to cool down to 75° C. and was stirred at this temperature for 2 hrs. The mixture was allowed to cool down to 20-20° C. and was stirred overnight. The solid was collected by filtration (glass frit, S3), washed twice with 15 ml of cold (<10° C.) 2-propanol and dried (80° C., 100 torr, $N_2$ strip, 2 hrs). 13.70 g (80% of the theoretical yield) of methyl 4-(7-(6-cyano-5-(trifluoromethyl)pyridin-3-yl)-8-oxo-6-thioxo-5,7-diazaspiro[3.4]octan-5-yl)-2-fluorobenzoate (99.62% purity (HPLC in, 275 nm) was obtained.

XRPD pattern of obtained solid corresponds to XRPD pattern depicted in FIG. 1.

Example 4: Preparation of Apalutamide, Compound of Formula (1)

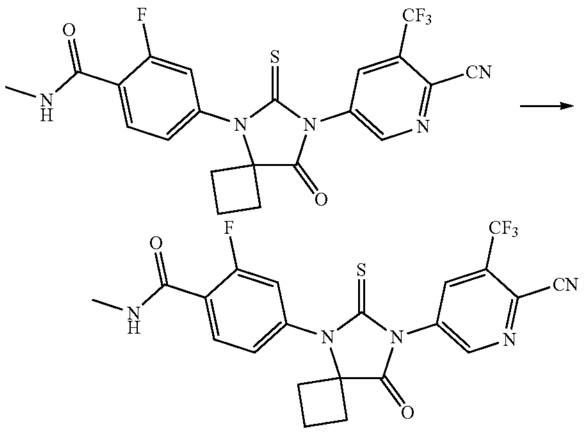

A mixture of 3 g of methyl 4-(7-(6-cyano-5-(trifluoromethyl)pyridin-3-yl)-8-oxo-6-thioxo-5,7-diazaspiro[3.4]octan-5-yl)-2-fluorobenzoate in 5 ml of tetrahydrofurane was added to a pre-cooled (0-4° C.) 14.47 ml of solution of methylamine in water (40% solution) during 10 minutes, while the temperature of the reaction mixture was kept at 0-2° C. The resulting solution was stirred for additional 2 hours at 0° C. The reaction was quenched with 26 ml of 6M HCl in isopropylalcohol while precipitation occurred. The formed solid was collected by filtration, subsequently washed with 10 ml of water, suction dried on air and then dried in vacuum drier (80° C., 100 torr, N2 strip, 16 hours). 2.62 g of Apalutamide (86% of theoretical yield) was obtained, 98.15% purity (HPLC, IN, 275 nm).

Example 5: Preparation of Solid Form of Apalutamide, Form 3

1 g of amorphous Apalutamide was mixed with 10 ml of water. The suspension was stirred for 1 hour at 20-25° C. and filtered off. Solid mass was dried at vacuum 18 h at 60° C. to provide Apalutamide Form 3 in quantitative (almost 100%) yield.

XRPD pattern of obtained solid corresponds to XRPD pattern depicted in FIG. 4. DSC pattern of obtained solid corresponds to DSC pattern depicted in FIG. 5. TGA pattern of obtained solid corresponds to TGA pattern depicted in FIG. 6.

Example 6: Preparation of Solid Form of Apalutamide, Form 3

APM Form 7 was exposed to 40° C. and 75% of relative humidity (or 55° C./90% RH) for 1 month to provide solid Form 3 of Apalutamide. XRPD pattern of obtained solid corresponds to XRPD pattern depicted in FIG. 4. DSC pattern of obtained solid corresponds to DSC pattern depicted in FIG. 5. TGA pattern of obtained solid corresponds to TGA pattern depicted in FIG. 6.

Example 7: Preparation of Solid Form of Apalutamide 1-methoxy-2-propanol Solvate, Form 5

1 g of amorphous Apalutamide was mixed with 8 ml of 1-methoxy-2-propanol. The reaction mixture was stirred for 3 hours at 25-27° C. The suspension was filtered, the filter cake was washed with 1 ml of 1-methoxy-2-propanol and dried in the vacuum drier (25° C., 130 mbar, $N_2$ bleed, 2 hour) to provide 0.71 g of solid Form 5 of Apalutamide 1-methoxy-2-propanol solvate. XRPD pattern of obtained solid corresponds to XRPD pattern depicted in FIG. 7. DSC pattern of obtained solid corresponds to DSC pattern depicted in FIG. 8. TGA pattern of obtained solid corresponds to TGA pattern depicted in FIG. 9.

Example 8: Preparation of Solid Form of Apalutamide Methyl Isobutyl Ketone Solvate, Form 6

50 mg of amorphous Apalutamide was mixed with 305 mg of methyl isobutyl ketone. The mixture was heated to 60° C. and left cooled to 25-27° C. and stirred for 10 hours at 25-27° C. The suspension was filtered and the filter cake was dried in the vacuum drier (25° C., 130 mbar, $N_2$ bleed, 2 hour) to provide 63 mg of solid Form 6 of Apalutamide methyl isobutyl ketone solvate. XRPD pattern of obtained solid corresponds to XRPD pattern depicted in FIG. 10. DSC pattern of obtained solid corresponds to DSC pattern depicted in FIG. 11. TGA pattern of obtained solid corresponds to TGA pattern depicted in FIG. 12.

Example 9: Preparation of Solid Form of Apalutamide 2-propanol Solvate, Form 7

0.30 g of Apalutamide was mixed with 6 ml of 2-propanol (2-PrOH). The mixture was heated to 70° C. and stirred at this temperature for 0.5 h. The mixture was left cooled to ambient temperature (20-25° C.) and stirred at this temperature for 12 hours. The suspension was filtered, the filter cake was washed with 2 ml of 2-PrOH and was dried 3 h on air to provide 0.34 g of solid Form 7 of Apalutamide 2-propanol solvate. XRPD pattern of obtained solid corresponds to XRPD pattern depicted in FIG. 13. DSC pattern of obtained solid corresponds to DSC pattern depicted in FIG. 14. TGA pattern of obtained solid corresponds to TGA pattern depicted in FIG. 15.

Example 10: Preparation of Solid Form of Apalutamide 2-propanol Solvate, Form 7

0.30 g of amorphous Apalutamide was mixed with 6 ml of 2-propanol (2-PrOH). The mixture was stirred at ambient temperature (20-25° C.) stirred for 12 hours. The suspension was filtered, the filter cake was washed with 2 ml of 2-PrOH and was dried 3 h on air to provide 0.32 g of solid Form 7 of Apalutamide 2-propanol solvate. XRPD pattern of obtained solid corresponds to XRPD pattern depicted in FIG. 13. DSC pattern of obtained solid corresponds to DSC pattern depicted in FIG. 14. TGA pattern of obtained solid corresponds to TGA pattern depicted in FIG. 15.

Example 11: Preparation of Compound of Formula (5) ($R_1$: $CH_3$), 1-((3-fluoro-4-(methoxycarbonyl)phenyl)amino)cyclobutane-1-carboxylic Acid

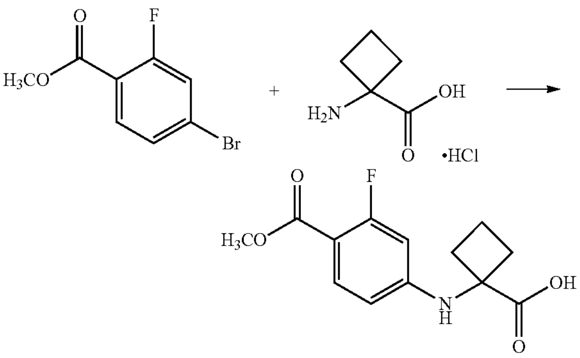

12 kg of dimethylsulfoxide (DMSO) was mixed with 3.28 kg of 1-aminocyclobutane-1-carboxylic acid hydrochloride. The mixture was heated at 40-45° C. until full dissolution, them cooled to 30° C. Afterwards, 5.77 kg of potassium carbonate was slowly (in the course of 20 minutes) added and the mixture was stirred at the same temperature for 15 minutes. 382 g of copper (I) chloride and 3.6 kg of methyl 4-bromo-2-fluorobenzoate and 1.9 kg of DMSO were added. The mixture was then heated to 100° C. and stirred for 2.5 hours. After the reaction was complete the mixture was cooled to 8° C., then mixture of 6.19 kg of concentrated hydrochloric acid (36%) and 12.2 kg of water was slowly (in the course of 90 minutes) added while temp. was kept below 22° C. After the addition, the mixture was stirred at 15-25° C. for 30 minutes and filtered. The filtration cake was washed with 4×7.2 kg of water and dried at 45° C. for 6 hours to give the 3.61 kg of title product, purity 97.8% (HPLC IN).

Example 12: Preparation of Compound of Formula (2) (R1: CH3, R2:CH3), methyl 2-fluoro-4-((1-(methoxycarbonyl)cyclobutyl)amino)benzoate

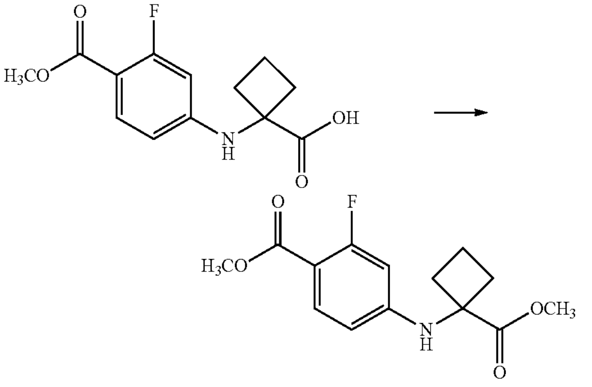

7 kg of 1-((3-fluoro-4-(methoxycarbonyl)phenyl)amino) cyclobutane-1-carboxylic acid (7.0 Kg) was mixed with 22.1 kg of methanol. The mixture was heated to 40° C., then 2.83 kg of concentrated (96%) sulfuric acid was added. The mixture was heated to 65° C. and stirred for 3 hours. The mixture was cooled to 35° C., followed by addition of 5.9 kg of triethylamine and 10.5 kg of water. The mixture was cooled to −2° C., stirred for 20 minutes and filtered. The filtration cake was washed with 2×8.8 kg of 50% aqueous methanol and dried at room temperature for 5 hours to give 6.91 kg of title product with purity 99.8% (HPLC IN).

Figure 18:
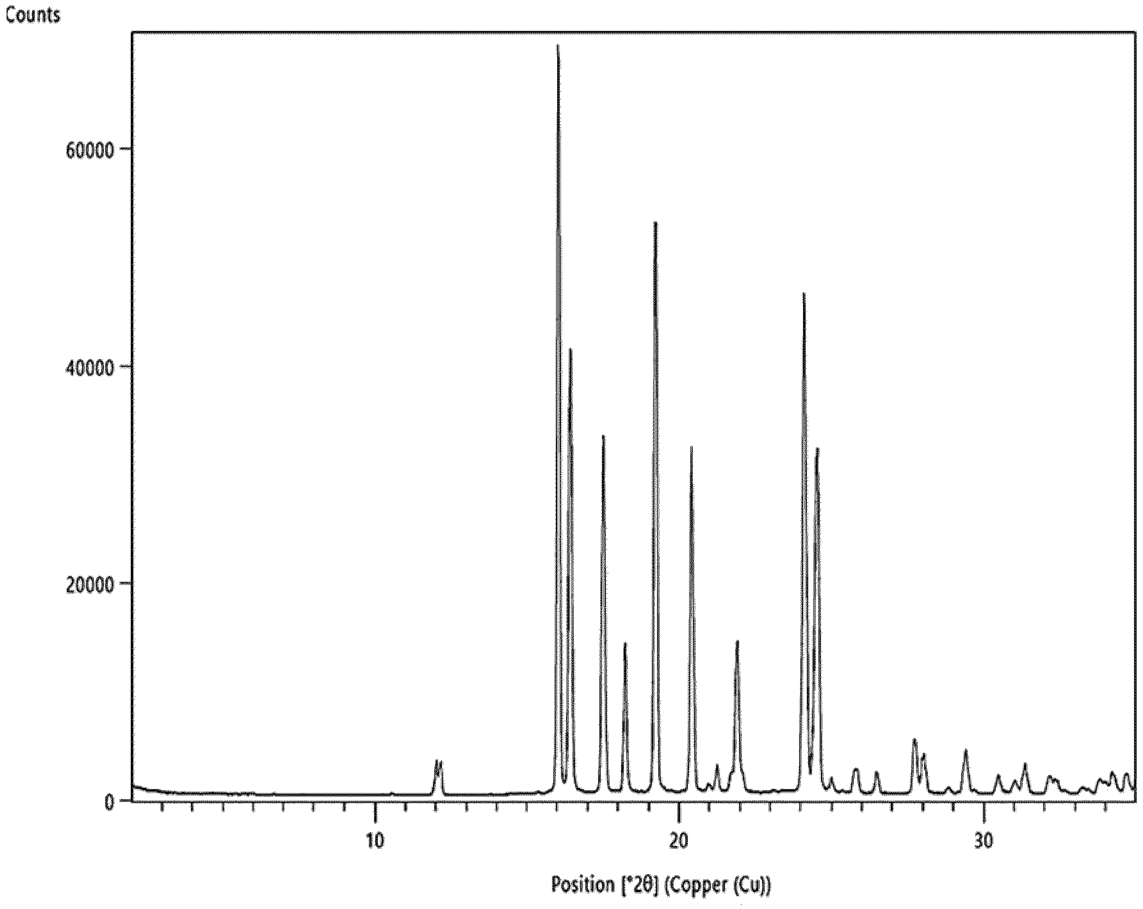
FIG. 18: XRPD pattern of solid form of Compound (2A), Form A, prepared according to Example 12.

XRPD pattern of obtained solid corresponds to XRPD pattern depicted in FIG. 18.

Example 13: Preparation of Compound of Formula (4) (R1: CH3), methyl 4-(7-(6-cyano-5-(trifluoromethyl)pyridin-3-yl)-8-oxo-6-thioxo-5,7-diazaspiro [3.4]octan-5-yl)-2-fluorobenzoate

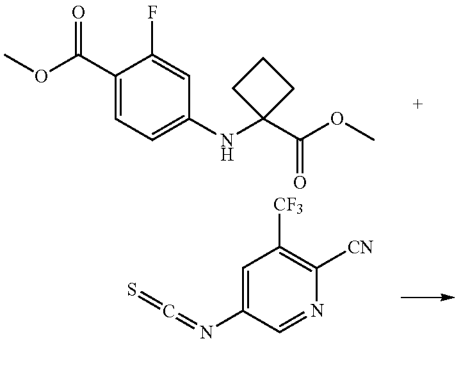

-continued

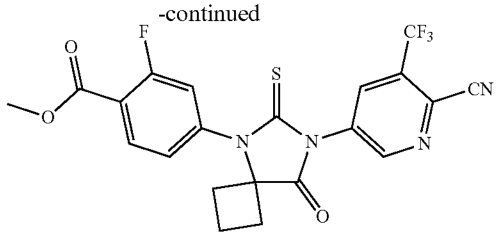

5 kg of methyl 2-fluoro-4-((1-(methoxycarbonyl)cyclobutyl)amino)benzoate was dissolved in 14 kg of tetrahydrofuran (THF). The mixture was cooled to −5° C., followed by addition of 13.92 kg of lithium bis(trimethylsilyl)amide (LiHMDS) (20% solution in THF). Temperature during the addition was kept below 5° C. When the addition was finished, the mixture was stirred for 15 minutes and cooled to −9° C. Then solution of 4.24 kg of 5-isothiocyanato-3-(trifluoromethyl)picolinonitrile in 5.5 kg of tetrahydrofuran was added slowly (in the course of 20 minutes), while keeping the temperature below 0° C. After the addition was finished, the mixture was cooled to −9° C. To the mixture a mixture of 3.6 kg of concentrated (36%) hydrochloric acid and 16.8 kg of water was added. The mixture was then heated to 30° C. and the bottom water phase was separated. The organic phase was then washed with 15 kg of 20% aq. NaCl. The organic extract was the concentrated under vacuum to approximate volume 15 l, and then switched to methanol using sequential addition and distillation of 31.7 kg of methanol and finally concentrating the mixture to approximate volume 35 l. 11.8 kg of isopropanol was added and the mixture was heated under reflux for 20 minutes, then cooled to −5° C., stirred for 30 minutes and filtered. The filtration cake was washed with 2×13 kg of 60% aqueous methanol and dried at 45° C. for 6 hours to give 7 kg of the title product, purity 99.6% (HPLC IN).

Example 14: Preparation of Apalutamide, Compound of Formula (1)

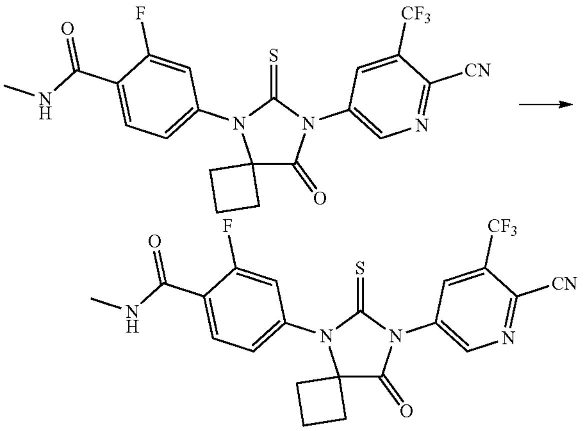

20.3 kg of Methylamine (40% solution in water) was cooled to 3° C. A solution of 5 kg of methyl 4-(7-(6-cyano-5-(trifluoromethyl)pyridin-3-yl)-8-oxo-6-thioxo-5,7-diazaspiro [3.4]octan-5-yl)-2-fluorobenzoate in 12.7 kg of 2-methyl tetrahydrofurane (2Me-THF) was charged slowly during 5 minutes. The mixture was then stirred at 4-5° C. for 4.5 hours.

A solution of 15.4 kg of glacial acetic acid in 13.4 kg of water was added slowly (in the course of 90 minutes), while the temperature of the mixture was controlled below 20° C. After the addition the mixture was heated to 30° C. and the bottom water phase was separated. The organic phase was mixed with 20 kg of 20% aqueous $K_2CO_3$, stirred at 30° C. for one minute and then the bottom water phase was separated. The remaining organic phase was washed again under the same conditions with 20 kg of 6% aqueous $K_2CO_3$. To the organic phase was a solution of 10 kg of 2% aqueous acetic acid was charged into the mixture and the reactor content was heated up to 60° C. 3.9 kg of 2-propanol was added and the bottom water phase was separated. The organic phase was mixed with additional 27.5 kg of 2-propanol and the mixture was heated to reflux, stirred for 15 minutes and then cooled to −5° C. by linear temp ramp during 3 hours. Afterwards, the mixture was stirred for 30 minutes, filtered and the filtration cake was washed with 2×7.8 kg of cold 2-propanol. The obtained crystalline solid was dried at 45° C. for 6 hours to yield 4.6 Kg of crude Apalutamide form 7 (HPLC purity 99.86%). XRPD pattern of obtained solid corresponds to XRPD pattern depicted in FIG. 1. DSC pattern of obtained solid corresponds to DSC pattern depicted in FIG. 2. TGA pattern of obtained solid corresponds to TGA pattern depicted in FIG. 3.

Example 15: Preparation of Solid Form of Apalutamide, Compound of Formula (1)

4.6 kg of Apalutamide was mixed with 28.3 kg of 2-propanol and 15.3 kg of methanol. The mixture was heated and stirred at reflux for 10 minutes until full dissolution of Apalutamide. Afterwards, the solution was cooled to −8° C. by linear temp ramp during 3 hours. The mixture was stirred for 30 minutes, filtered and the filtration cake was washed with cold 2×7.3 kg of 2-propanol. The obtained crystalline solid was dried at 45° C. for 6 hours to yield 4.2 Kg of final Apalutamide form 7 (HPLC purity 99.90%). XRPD pattern of obtained solid corresponds to XRPD pattern depicted in FIG. 13. DSC pattern of obtained solid corresponds to DSC pattern depicted in FIG. 14. TGA pattern of obtained solid corresponds to TGA pattern depicted in FIG. 15.

The invention claimed is:

1. A process for preparation of Compound (1) or a salt thereof, (1)

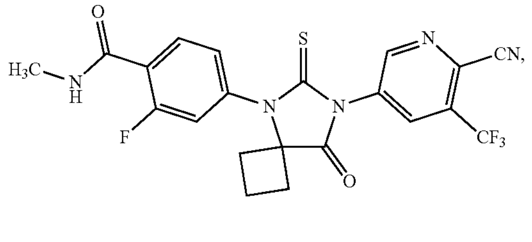

which comprises:

a) reacting Compound (2) with Compound (3) in the presence of a non-nucleophilic base to obtain Compound (4), wherein the $pK_a$ value of conjugated acid formed from the non-nucleophilic base is higher than 25

(2)

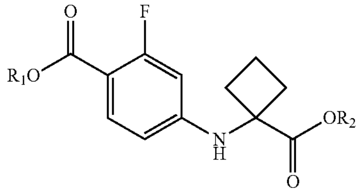

(3)

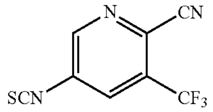

(4)

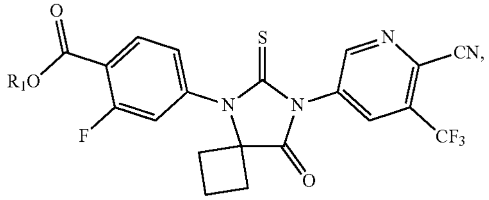

wherein $R_1$ is selected from $C_1$-$C_6$ alkyl or substituted $C_1$-$C_6$ alkyl or aryl or substituted aryl, $R_2$ is selected from alkyl or substituted alkyl or aryl or substituted aryl or $C(O)R_3$ or $C(O)OR_3$, and $R_3$ is selected from $C_1$-$C_6$ alkyl or substituted $C_1$-$C_6$ alkyl or aryl or substituted aryl; and b) transforming Compound (4) into Compound (1) or a salt thereof.

2. The process according to claim 1 wherein $R_1$ and $R_2$ are selected from $C_1$-$C_6$ alkyl or substituted $C_1$-$C_6$ alkyl.

3. The process according to claim 1 wherein $R_1$ and $R_2$ are $CH_3$.

4. The process according to claim 1 wherein the non-nucleophilic base is selected from lithium bis(trimethylsilyl)amide or sodium bis(trimethylsilyl)amide or potassium bis(trimethylsilyl)amide or sodium hydride or potassium hydride or lithium diisopropylamide or lithium diethylamide or lithium dicyclohexylamide or lithium 2,2,6,6-tetramethylpiperidine or Hauser bases or turbo-Hauser bases.

5. The process according to claim 4 wherein the base is lithium bis(trimethylsilyl)amide or sodium bis(trimethylsilyl)amide or potassium bis(trimethylsilyl)amide.

6. The process according to claim 1 where the reaction step a) is performed in dimethylformamide or tetrahydrofuran or 2-methyltetrahydrofuran.

7. The process according to claim 1 wherein the transforming step b) comprises reacting compound (4) with methylamine or a salt thereof.

8. The process according to claim 1, which further comprises preparing said Compound (2) by a process that comprises reacting Compound (5) with an acid and an alcohol $R_2OH$, wherein $R_2$ is selected from alkyl or substituted alkyl or aryl or substituted aryl or $C(O)R_3$ or $C(O)OR_3$, and $R_3$ is selected from $C_1$-$C_6$ alkyl or substituted $C_1$-$C_6$ alkyl or aryl or substituted aryl (5)

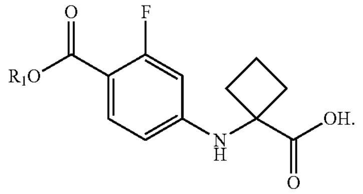

9. The process according to claim 8 wherein the alcohol $R_2OH$ is methanol.

10. The process according to claim 1, which further comprises preparing said Compound (5) by reacting Compound (6) and Compound (7) or a salt thereof under a protective gas wherein the protective gas is streamed above the reaction mixture:

(6)

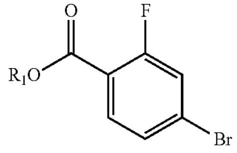

(7)

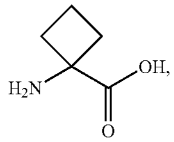

wherein $R_1$ is selected from $C_1$-$C_6$ alkyl or substituted $C_1$-$C_6$ alkyl or aryl or substituted aryl.

11. The process according to claim 10 wherein the protective gas is argon or nitrogen.

12. The process according to claim 10 wherein the protective gas is streamed above the reaction mixture at a rate between 1 and 100 l/minute.

13. The process according to claim 9 which further comprises obtaining said Compound (2) as a solid form, and said Compound (2) is a Compound (2A), (2A)

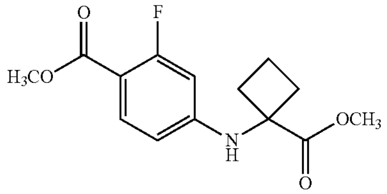

and is obtained as a crystalline solid form characterized by XRPD pattern having 2θ values 10.2°, 14.5° and 17.4° 2θ (±0.2 degrees 2θ).

14. The process according to claim 13 wherein said crystalline form is characterized by XRPD pattern having 2θ values 10.2°, 14.5°, 15.2°, 17.4° and 19.0° 2θ (±0.2 degrees 2θ).

* * * * *